United States Patent
Hoh et al.

(10) Patent No.: US 7,713,750 B2
(45) Date of Patent: May 11, 2010

(54) ABLATION BASED LASER MACHINING OF BIOMOLECULE PATTERNS ON SUBSTRATES

(75) Inventors: Jan Hoh, Baltimore, MD (US); William F. Heinz, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/755,187

(22) Filed: May 30, 2007

(65) Prior Publication Data

US 2007/0281310 A1 Dec. 6, 2007

Related U.S. Application Data

(60) Provisional application No. 60/809,625, filed on May 31, 2006.

(51) Int. Cl.
| | |
|---|---|
| *C12Q 1/00* | (2006.01) |
| *G01N 21/00* | (2006.01) |
| *G01N 1/28* | (2006.01) |
| *G01N 33/53* | (2006.01) |
| *G01N 33/543* | (2006.01) |
| *G01N 33/552* | (2006.01) |
| *C08J 7/04* | (2006.01) |
| *C08J 7/18* | (2006.01) |
| *C08F 2/48* | (2006.01) |
| *B05D 3/06* | (2006.01) |
| *B01J 19/08* | (2006.01) |

(52) U.S. Cl. ............... 436/518; 435/4; 435/7.1; 436/527; 436/807; 422/57; 427/2.11; 427/457; 427/504; 427/508; 427/510; 427/552; 427/554; 427/555; 427/581

(58) Field of Classification Search .............. 435/4, 435/7.1; 436/518, 527, 807; 422/57; 427/2.11, 427/457, 504, 508, 510, 552, 554, 555, 581
See application file for complete search history.

(56) References Cited

U.S. PATENT DOCUMENTS

| 4,785,806 A | 11/1988 | Deckelbaum |
| 4,802,951 A | 2/1989 | Clark et al. |
| RE33,581 E | 4/1991 | Nicoli et al. |
| 5,079,600 A | 1/1992 | Schnur et al. |
| 5,143,854 A | 9/1992 | Pirrung et al. |

(Continued)

FOREIGN PATENT DOCUMENTS

WO    WO 98/23957    6/1998

OTHER PUBLICATIONS

Harnett et al. "Low-energy electron-beam patterning of amine-functionalized self-assembled monolayers," Applied Physics Letters. vol. 76, No. 17 (2000) 2466-2468.*

(Continued)

*Primary Examiner*—Mark L Shibuya
*Assistant Examiner*—Jacqueline Diramio
(74) *Attorney, Agent, or Firm*—Barnes & Thornburg LLP; Alice O. Martin

(57) ABSTRACT

A method for patterning a one or more biomolecules on a substrate that includes coating the substrate with a coating of the one or more biomolecules, applying a laser to the coating, and ablating a portion of the one or more biomolecules with the laser in a predetermined pattern.

15 Claims, 7 Drawing Sheets

U.S. PATENT DOCUMENTS

| | | | |
|---|---|---|---|
| 5,202,227 | A | 4/1993 | Matsuda et al. |
| 5,324,591 | A | 6/1994 | Georger, Jr. et al. |
| 5,352,582 | A | 10/1994 | Lichtenwalter et al. |
| 5,470,739 | A | 11/1995 | Akaike et al. |
| 5,776,748 | A | 7/1998 | Singhvi et al. |
| 6,103,479 | A | 8/2000 | Taylor |
| 6,104,484 | A * | 8/2000 | Nagata et al. ............... 356/246 |
| 6,180,239 | B1 | 1/2001 | Whitesides et al. |
| 6,215,550 | B1 | 4/2001 | Baer et al. |
| 6,329,209 | B1 | 12/2001 | Wagner et al. |
| 6,368,838 | B1 | 4/2002 | Singhvi et al. |
| 6,406,921 | B1 | 6/2002 | Wagner et al. |
| 6,773,903 | B2 | 8/2004 | Bova |
| 6,776,094 | B1 | 8/2004 | Whitesides et al. |
| 6,893,850 | B2 | 5/2005 | Ostuni et al. |
| 7,067,306 | B2 | 6/2006 | Singhvi et al. |
| 7,223,534 | B2 * | 5/2007 | Kaylor et al. .................. 435/5 |
| 2003/0100030 | A1 * | 5/2003 | Nadaoka et al. .............. 435/7.9 |
| 2004/0224321 | A1 | 11/2004 | Nicolau et al. |
| 2005/0053949 | A1 | 3/2005 | Silin |

OTHER PUBLICATIONS

Aguilar et al., "Direct micro-patterning of biodegradable polymers using ultraviolet and femtosecond lasers," *Biomaterials*, 26: 7642-7649 (2005).
Berg et al., "Controlling Mammalian Cell Interactions on Patterned Polyelectrolyte Multillayer Surfaces," *Langmuir*, 20: 1362-1368 (2004).
Blawas et al., "Protein patterning," *Biomaterials*, 19: 595-609 (1998).
Burgemeister, "New Aspects of Laser Microdissection in Research and Routine," *Journal of Histochemistry & Cytochemistry*, 53 (3): 409-412 (2005).
Chen et al., "Geometric Control of Cell Life and Death," *Science*, 276: 1425-1428 (1997).
Chen et al., "Micropatterned Surfaces for Control of Cell Shape, Position, and Function," *Biotechnol. Prog.*, 14: 356-363 (1998).
Clark et al., "Cell guidance by micropatterned adhesiveness in vitro," *Journal of Cell Science*, 103: 287-292 (1992).
Cornea et al., "[1] Comparison of Current Equipment," *Methods in Enzymology*, 356: 3-12 (2002).
Curran et al., "Laser capture microscopy," *J. Clin. Pathol.; Mol. Pathol.*, 53: 64-68 (2000).
Dickson et al., "Molecular Mechanisms of Axon Guidance," *Science*, 298: 1959-1964 (2002).
Dike et al., "Geometric Control of Switching Between Growth, Apoptosis, and Differentiation During Angiogenesis Using Micropatterned Substrates," In Vitro *Cell. Dev. Biol.-Animal*, 35: 441-448 (1999).
Dillmore et al., "A Photochemical Method for Patterning and Immobilization of Ligands and Cells to Self-Assembled Monolayers," *Langmuir*, 20: 7223-7231 (2004).
Giordano et al., "B-cell size influences glucose-stimulated insulin secretion," *Cell Physiology*, 265 (2): C358-C364 (1993).
Huet et al., "Extracellular matrix regulates ovine granulose cell survival, proliferation and steroidgenesis: relationships between cell shape and function," *Journal of Endocrinology*, 169: 347-360 (2001).
Ingber, "Extracellular matrix as a solid-state regulator in angiogenesis; identification of new targets for anti-cancer therapy," *Seminars in Cancer Biology*, 3: 57-63 (1992).
Jung et al., "Topographical and Physicochemical Modification of Material Surface to Enable Patterning of Living Cells," *Critical Reviews in Biotechnology*, 21 (2): 111-154 (2001).
Kandere-Grzybowska et al., "Molecular dynamics imaging in micropatterned living cells," *Nature Methods*, 2 (10): 739-741 (2005).

Lippert et al., "Chemical and Spectroscopic Aspects of Polymer Ablation: Special Features and Novel Directions," *Chem. Rev.*, 103: 453-485 (2003).
Liu et al., "3D femtosecond laser patterning of collagen for directed cell attachment," *Biomaterials*, 26: 4597-4605 (2005).
Micke et al., "Laser-Assisted Cell Microdissection Using the PALM System," *Methods in Molecular Biology*, 293: 151-166 (2005).
Paltauf et al., "Photomechnical Processes and Effects in Ablation," *Chem. Rev.*, 103: 487-518 (2003).
Park et al., "Integration of Cell Culture and Microfabrication Technology," *Biotechnol. Prog.*, 19: 243-253 (2003).
Pesen et al., "Electron beam patterning of fibronectin nanodots that support focal adhesion formation," *Soft Matter*, 3: 1280-1284 (2007).
Recknor et al., "Directed growth and selective differentiation of neural progenitor cells on micropatterned polymer substrates," *Biomaterials*, 27: 4098-4108 (2006).
Rosso et al., "From Cell-ECM Interactions to Tissue Engineering," *Journal of Cellular Physiology*, 199: 174-180 (2004).
Rundqvist et al., "High Fidelity Functional Patterns of an Extracellular Matrix Protein by Electron Beam-Based Inactivation," *J. Am. Chem. Soc.*, 129: 59-67 (2007).
Shannon, "A Mathematical Theory of Communication," *The Bell System Technical Journal*, 27: 379-423, 623-656 (1948).
Srinivasan, "Ablation of Polymers and Biological Tissue by Ultraviolet Lasers," *Science*, 234 (4776): 559-565 (1986).
Thery et al., "The extracellular matrix guides the orientation of the cell division axis," *Nat. Cell. Biol.*, 7 (10): 947-953 (2005).
Thery et al., "Anisotropy of cell adhesive microenvironment governs cell internal organization and orientation of polarity," *PNAS*, 103 (52): 19771-19776 (2006).
Vaidya et al., "Computer-Controlled Laser Ablation: A Convenient and Versatile Tool for Micropatterning Biofunctional Synthetic Surfaces for Appplications in Biosensing and Tissue Engineering," *Biotechnol. Prog.*, 14: 371-377 (1998).
Vogel et al., "Mechanisms of Pulsed Laser Ablation of Biological Tissues," *Chem. Rev.*, 103: 577-644 (2003).
Vogt et al., "Micropatterned Substrates for the Growth of Functional Neuronal Networks of Defined Geometry," *Biotechnol. Prog.*, 19: 1562-1568 (2003).
Vogt et al., "Impact of micropatterned surfaces on neuronal polarity," *Journal of Neuroscience Methods*, 134: 191-198 (2004).
Welch et al., "Laser Thermal Ablation," *Photochemistry and Photobiology*, 53 (6): 815-823 (1991).
Wittliff et al., "[2] Laser Capture Microdissection and Its Applications in Genomics and Proteomics," *Methods in Enzymology*, 356: 12-25 (2002).
Yim et al., "Significance of synthetic nanostructures in dictating cellular response," *Nanotechnology*, 1: 10-21 (2005).
Bastiaans, "Gabor Expansion of a Signal into Gaussian Elementary Signals," *Proceedings of the IEEE*, 68(4): 538-539 (1980).
de Wolf, D.A., "Gaussian Decomposition of Beams and Other Functions," *Journal of Applied Physics*, 65(12): 5166-5169 (1989).
Duarte, "Newton, Prisms, and the "Opticks" of Tunable Lasers," *Optics & Photonics News*, 25-28 (May 2000).
Duarte, "Organic Dye Lasers Brief History and Recent Developments," *Optics & Photonics News*, 20-25 (Oct. 2003).
Gabor, "Theory of Communication," *The Journal of the Institute of Electrical Engineers*, 93(21)(Part III): 429-457 (1946).
Hammarback et al., "Guidance of Neurite Outgrowth by Pathways of Substratum-Adsorbed Laminin," *Journal of Neuroscience Research*, 13: 213-220 (1985).
Janssen, "Gabor Representation of Generalized-Functions," *Journal of Mathematical Analysis and Applications*, 83(2): 377-394 (1981).
Piliarik et al., "Surface Plasmon Resonance Biosensing", *Methods in Molecular Biology: Biosensors and Biodetection*, Chapter 5, vol. 503, Humana Press, pp. 65-88 (2009).

* cited by examiner

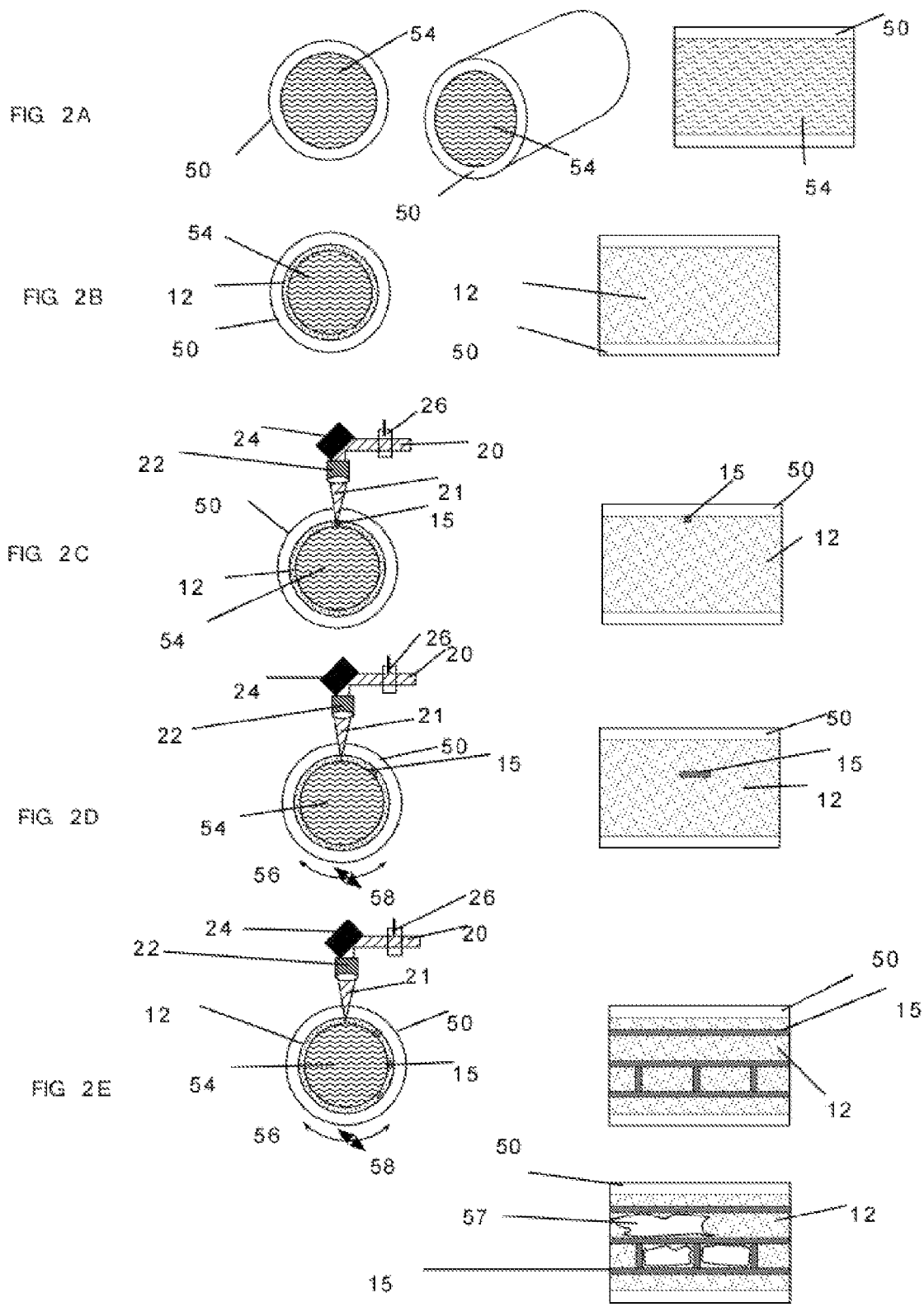

82
85

ABLATION BASED LASER MACHINING OF BIOMOLECULE PATTERNS ON SUBSTRATES

This application is a non-provisional claiming priority under 35 U.S.C. §119(e) to U.S. Provisional Patent Application No. 60/809,625 filed May 31, 2006, which is expressly incorporated herein by reference in their entirety.

BACKGROUND

Methods and compositions for patterning biological material on a substrate are described, including a method for ablating biomolecules on a substrate with a laser to form a pattern. Patterned substrates and applications thereof are also described.

Control of the position or distribution of biologically active molecules or biomolecules on a substrate is important for a wide range of scientific and technological applications. This controlled positioning has commonly become known as "patterning" of these molecules. For example, the patterning of DNA oligonucleotides on a glass substrate is used to make microarrays; similarly the patterning of proteins on a substrate is used to make protein arrays. These types of arrays have a range of analytical and diagnostic applications. In cell biology, substrates patterned with extracellular matrix proteins are used to control the shape, position and behavior of cells.

To pattern biologically active molecules, a wide range of methods have been developed. These methods can be divided into two classes: self-assembled patterning and directed patterning. In self-assembled patterning the physical chemical properties of a molecule or combination of molecules are exploited under specific conditions to produce distributions of molecules with known non-random organizational properties. For example, a self-assembled monolayer of alkanethiols on gold will often have a high degree of order that results from intermolecular interactions between the components of the molecules. This order is a pattern, and it in turn can be used to create patterns of other molecules. Also, colloidal particles adsorbed onto a surface can have varying degrees of order that can be used to create patterns.

In directed patterning, the position of molecules is controlled by information that is brought in from the outside, such as a mask or a template. Directed patterning methods can in turn be divided into two types: lithographic approaches and writing approaches. Lithographic approaches include methods where a physical template such as a mask or a mold is used to transfer a pattern to an object. Examples include conventional photolithography and microcontact printing. In contrast, writing approaches use a serial approach to transfer a pattern, typically from a computer-based representation such as a CAD (computer assisted design) drawing, to an object. Electron beam lithography, despite its name, is a writing approach, by the definition used here. In general, lithographic approaches are good for producing many copies of the same pattern; writing approaches are good for producing unique patterns, for producing a large number of different patterns, or for changing patterns quickly.

As noted above, there are a wide range of applications for patterning proteins and other biomolecules. One area that has become more important over the past decade is patterning of proteins for cell biological and related applications. In vitro cell culture was developed to facilitate the study and the biomedical and industrial uses of cells outside of an animal. During the last century cell culture techniques and materials have been refined to more accurately reflect the in vivo environment of the cells, to provide analytically and diagnostically informative responses from cells, and to more efficiently grow cells for research and industrial biomedical uses. One aspect of the cellular microenvironment that is not well-captured by traditional cell culture is the spatial heterogeneity of molecules in the extracellular environment. Molecules are not randomly arranged or uniformly arranged in the extracellular environment, and the spatial organization of the molecules influences cell structure and function.

SUMMARY

A method for patterning one or more biomolecules on a substrate includes coating the substrate with the one or more biomolecules; applying a laser onto the one or more of molecules; and ablating a portion of the one or more biomolecules with the laser in a predetermined pattern. The predetermined pattern has one or more ablated portions and one or more non-ablated portions on the substrate. The one or more ablated portions has less than 100% of biological function or activity, or biochemical function or activity of the one or more biomolecules on the substrate. The one or more non-ablated portions has one or more active or functional biomolecules of the one or more biomolecules on the substrate.

Ablating may include inactivating or rendering non-functional at least one of the one or more molecules with the laser such that the at least one of the one or more molecules remains on the substrate, removing one or more of the one or more biomolecules with the laser, breaking at least one covalent bond of the one or more biomolecules, changing a conformation of the one or more biomolecules, changing an orientation of the one or more biomolecules, or any combination thereof.

Applying the laser may include translating the substrate in one, two, or three dimensions to form the predetermined pattern, applying the laser further includes rotating the substrate around one, two, or three axes to form the predetermined pattern, or translating the substrate in one, two, or three dimensions and rotating the substrate around one, two, or three axes to form the predetermined pattern. Applying the laser may include directing electromagnetic radiation produced by the laser to the substrate via an optical system that includes, for example, of lenses, mirrors, filters, shutters, polarizers, and any other optical device that can modify the electromagnetic radiation or its path through space, and any combination thereof. The electromagnetic radiation may include continuous wave radiation or pulsed radiation. Applying the laser may include modulating the power, the pulse width, the pulse frequency, the irradiance, the fluence, and any combination thereof of the electromagnetic radiation arriving at the substrate.

The one or more biomolecules may include proteins, peptides, nucleic acids, drugs, lipids, bioactive polymers, bioactive compounds, and any combination thereof. The one or more biomolecules are proteins that may include fibronectin, vitronectin, collagen, growth factors, cellular membrane proteins, intracellular proteins, extracellular matrix proteins, soluble proteins, signaling proteins, and any combination thereof. The one or more of biomolecules may be attached to a particle or colloid including, for example, quantum dots, superparamagnetic nanoparticles, dendrimers, glass or silica particles, liposomes, viruses or phage particles and analogous particles, and any combination thereof The substrate may include glass, polymeric material, silicon, plastic, rubber, metal, ceramic, any material that is not substantially destroyed or damaged by the laser, and any combination thereof. The material that is not substantially destroyed or damaged may include material that is not substantially destroyed or damaged when laser irradiation of an area of a substrate removes material to a depth of more than 1 nanometer, more than 3 nanometers, more than 5 nanometers, more than 10 nanometers, more than 25 nanometers, more than 50 nanometers, more than 100 nanometers, more than 500 nanometers, more than 1 micrometer, more than 5 micrometers, more than 10 micrometers, more than 50 micrometers, or more than 100 micrometer from a point in an area irradiated by the laser.

Coating the substrate may include adsorbing the one or more biomolecules on the substrate. Adsorbing the one or more biomolecules on the substrate may include covalently attaching to the substrate, electrostatically attaching to the substrate, hydrophobically attaching to the substrate, sterically attaching to the substrate, entropically attaching to the substrate, and any combination thereof. Coating the substrate may include one or more biomolecules covalently or non-convalently attached to the substrate via a coupling molecule of varying length. Coating the substrate may include coating a non-uniform substrate.

The laser may remove the at least one of the one or more biomolecules at a first dose and inactivate at least one of the one or more biomolecules at a second dose, and wherein the second dose is lower than the first dose. Ablating may include forming a microplasma and applying the microplasma to the portion of the one or more biomolecules, patterning a portion of the one or more biomolecules of one type of biomolecule in a combination of two or more types of biomolecules, transferring heat from the laser to the substrate, a solvent or medium above the substrate, at least one of the one or more biomolecules, and any combination thereof. The predetermined pattern may contain a gradient of inactivated biomolecules, a gradient of removed biomolecules, or a combination of gradients of inactivated and removed biomolecules. The gradient may include a change in an amount of activity or function of the one or more biomolecules per unit distance, unit area, or unit volume as a function of position on the substrate, and any combination thereof.

The substrate may be translucent, where applying the laser includes applying the laser through an exterior side of the substrate onto an opposing interior side of the substrate, wherein the interior side of the substrate has the one or more biomolecules applied thereon, and wherein said molecules are partially or fully ablated in the predetermined pattern.

The method may include backfilling the one or more ablated portions with a second one or more biomolecules.

The one or more biomolecules may be hydrated in a liquid or dry layer. The one or more biomolecules may be in an aqueous solvent environment or in a non-aqueous solvent environment.

A substrate coated with one or more biomolecules in a pattern includes a first portion on the substrate having a coating. The coating has the one or more biomolecules and one or more ablated portions on the substrate. The one or more ablated portions has at least one dimension in the plane of the substrate from about at least 0.1 nanometer, at least 1 nanometer, at least 10 nanometers, at least 100 nanometers, or at least 250 nanometers to 1 meter. One or more non-ablated portions on the substrate has at least one dimension in the plane of the substrate from about at least 0.1 nanometer, at least 1 nanometer, at least 10 nanometers, at least 100 nanometers, or at least 250 nanometers to 1 meter. The one or more ablated portions have less than 100% of biological function or activity, or biochemical function or activity of the one or more biomolecules on the substrate.

The substrate coated with the one or more biomolecules may be a microscope coverslip, microscope slide, petri dish, tissue culture flask, biomedical implant, test tube, eppendorf tube, diagnostic assay, a biochip, a protein/nucleic acid biochip sensor, a cell-based sensor, a lab-on-a-chip assay, a lab-in-a-capillary assay, a cell adhesion assay, a cell translocation/migration/invasion/chemotaxis assay, or a neuronal-guidance assay. The substrate may be non-flat. The one or more ablated portions have inactivated or non-functional biomolecules. The one or more ablated portions may include at least one of the one or more biomolecules having a broken covalent bond, having been removed, having a changed conformation, and having a changed orientation, and any combination thereof. The substrate may have an exterior side opposite an interior side, and wherein the interior side has the coating applied thereon. The one or more biomolecules may be hydrated by a thin liquid or dry layer. The one or more biomolecules may be in an aqueous environment or a non-aqueous environment. The one or more biomolecules include, for example, proteins, peptides, nucleic acids, drugs, lipids, bioactive polymers, bioactive compounds, and any combination thereof. One or more biomolecules may be covalently or non-convalently attached to the substrate via a coupling molecule of varying length. The one or more biomolecules may be attachable to the substrate and are sensitive to laser exposure. The one or more of protein biomolecules may include fibronectin, vitronectin, collagen, growth factors, cellular membrane proteins, intracellular proteins, extracellular matrix proteins, soluble proteins, signaling proteins, and any combination thereof. The one or more of biomolecules may be attached to a particle or colloid include quantum dots, superparamagnetic nanoparticles, dendrimers, glass or silica particles, liposomes, viruses or phage particles and analogous particles, and any combination thereof. The substrate may include silicon, plastic, rubber, metal, ceramic material, or any material that is not destroyed or damaged by the laser, and any combination thereof, wherein the material that is not substantially destroyed or damaged includes material that is not substantially destroyed or damaged when laser irradiation of an area of a substrate removes material to a depth of more than 1 nanometer, more than 3 nanometers, more than 5 nanometers, more than 10 nanometers, more than 25 nanometers, more than 50 nanometers, more than 100 nanometers, more than 500 nanometers, more than 1 micrometer, more than 5 micrometers, more than 10 micrometers, more than 50 micrometers, or more than 100 micrometers from a point in an area irradiated by the laser.

A patterned substrate coated with a one or more biomolecules includes a pattern obtainable by coating the substrate with the one or more biomolecules; applying a laser onto the one or more of molecules; and ablating a portion of the one or more biomolecules with the laser in a predetermined pattern. The predetermined pattern has one or more ablated portions and one or more non-ablated portions on the substrate. The one or more ablated portions has less than 100% of biological function or activity, or biochemical function or activity of the one or more biomolecules on the substrate. The one or more non-ablated portions has one or more active or functional biomolecules of the one or more biomolecules on the substrate.

BRIEF DESCRIPTION OF THE DRAWINGS

FIG. 2A is a cross-sectional view of a translucent tube having solvent present within an interior of the translucent tube, a front perspective view of the translucent tube having solvent present within the interior, and a side view of the translucent tube having solvent present within the interior;

FIG. 2B is a cross-sectional view of biomolecules coated on an interior surface of a translucent tube in the presence of solvent and a side view of the biomolecules coated on an interior surface of a translucent tube in the presence of solvent;

FIG. 2C is a schematic diagram of ablating biomolecules on an interior surface of a translucent tube in the presence of solvent with a laser system and a side view of ablated and non-ablated biomolecules on the interior surface of the translucent tube in the presence of solvent;

FIG. 2D is a schematic diagram of translating a laser with a mirror, activating and deactivating the laser with a shutter, and translating and/or rotating the translucent tube, and a side view of ablated and non-ablated biomolecules on an inside surface of the translucent tube in the presence of solvent;

FIG. 2E is a schematic diagram of applying a laser to predetermined areas of biomolecules while translating the laser with a mirror, activating and deactivating the laser with a shutter, and rotating and/or translating the translucent tube forming patterned biomolecules on an inside surface of the translucent tube, a side view of ablated and non-ablated biomolecules on the inside surface of the translucent tube in the presence of solvent in a pattern, and cultured adherent cells on the inside surface of the translucent tube that are influenced by the patterned biomolecules;

DETAILED DESCRIPTION

Figures 1A, 1B, 1C, 1D, 1E, 1F:
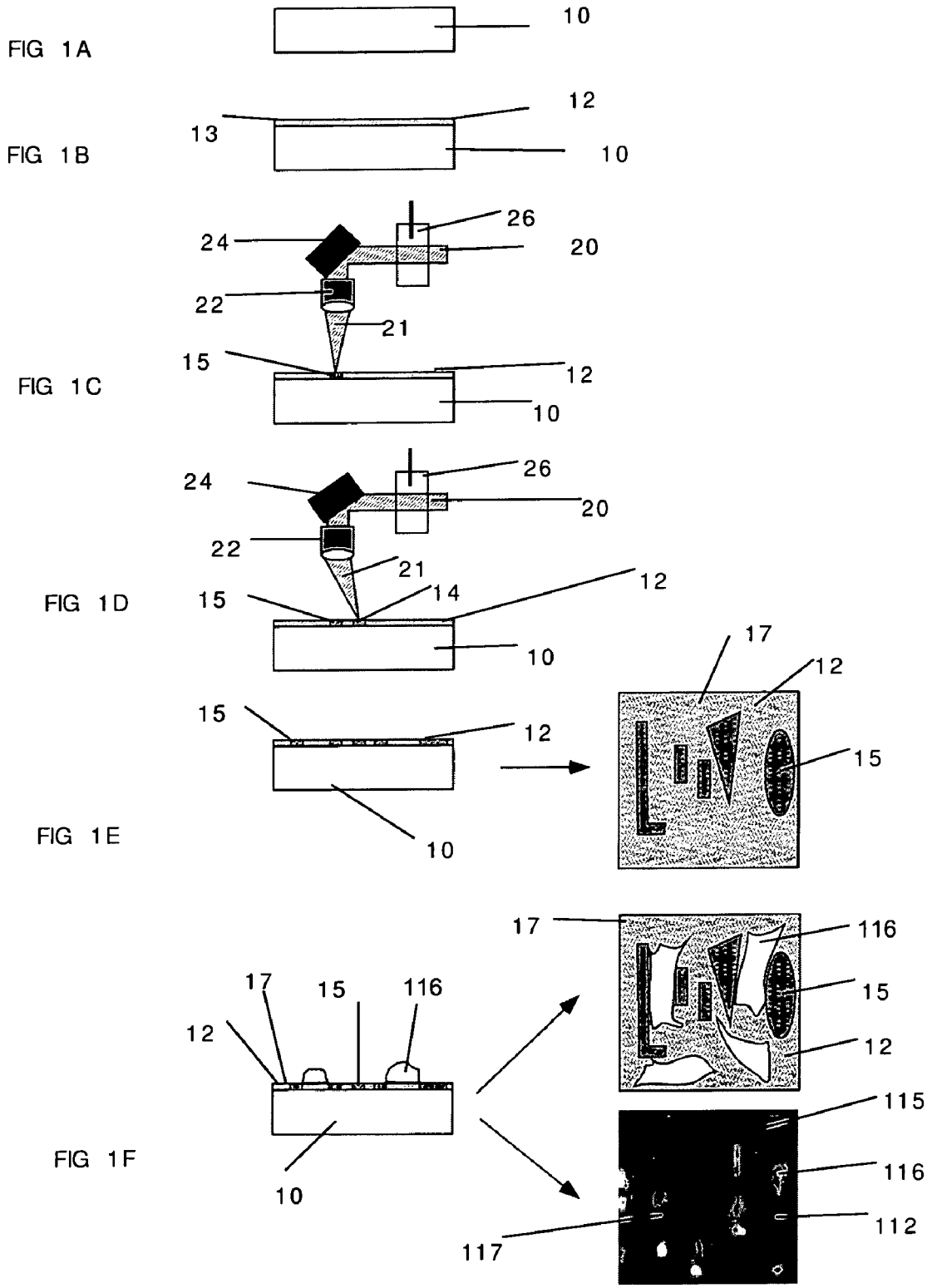
FIG. 1A is a side view of an illustrative substrate in accordance with the present disclosure.
FIG. 1B is a side view of an illustrative biomolecule coated substrate.
FIG. 1C is a schematic diagram of a laser system applying a laser to a biomolecule coated substrate.
FIG. 1D is a schematic diagram of a laser system translating and shuttering a beam onto a biomolecule coated substrate to form a pattern.
FIG. 1E is a side view of a surface having an arbitrary pattern of ablated biomolecules and non-ablated biomolecules on a surface and plan view of the surface having the arbitrary pattern of ablated biomolecules and non-ablated biomolecules on the surface.
FIG. 1F is a side view of cells grown on a surface, a plan view of cells grown on a surface within different shapes of ablated biomolecules and non-ablated biomolecules, and a plan view immunofluorescence light micrograph of cells grown within a rectangular pattern, where the active fibronectin is stained with an antibody against fibronectin, and the cells are stained with a non-specific membrane label. The fluorescence intensity of the fibronectin staining is proportional to the activity of the fibronectin; thus, the fibronectin activity in the pattern ranges from high (light areas) to low (dark areas)

While the present disclosure may be susceptible to embodiment in different forms, there are shown in the drawings, and herein will be described in detail, embodiments with the understanding that the present description is to be considered an exemplification of the principles of the disclosure and is not intended to limit the disclosure to the details of construction and the arrangements of components set forth in the following description or illustrated in the drawings.

Referring now to FIGS. 1A through 1F, a patterned substrate and a method for ablating biomolecules on a substrate with a laser to form a predetermined pattern including one or more ablated portions and one or more non-ablated portions are shown. Ablating removes or inactivates active portions or functional portions of biomolecules. Ablation can include a change in conformation of a biomolecule, a change in orientation of a biomolecule, a breaking of at least one covalent bond in a biomolecule, a removal at least one atom from one or more biomolecules and at most 100% of the one or more biomolecules, such that an activity or a function of the biomolecule or group of biomolecules is partially or fully lost. Biomolecules are any biologically active molecules or molecules that modify a function or an activity of a biological or biochemical entity.

As shown in FIG. 1A, a substrate 10 is shown. Substrate 10, for example, is glass, polymeric material, silicon, plastic, rubber, metal, ceramic material, and any material that is not destroyed or substantially damaged by laser irradiation, or any combination thereof. Substantial damage occurs when laser irradiation of an area of substrate 10 removes material to a depth of more than 1 nanometer (nm), more than 3 nm, more than 5 nm, more than 10 nm, more than 25 nm, more than 50 nm, more than 100 nm, more than 500 nm, more than 1 µm, more than 5 micrometer (µm), more than 10 µm, more than 50 µm, or more than 100 µm from some point in the area irradiated by the laser.

Substrate 10 may be a non-flat substrate or a three dimensional substrate selected from the group consisting of for example, a microfabricated substrate or device, Micro-Electro-Mechanical Systems (MEMS) devices, a Petri dish, a vascular stent, an auditory implant, and analogous devices. Substrate 10 may be an interior substrate or opposing side of a translucent material. Substrate 10 may be an interior substrate of a translucent material of a three-dimensional structure. Substrate 10 can be an interior substrate of a solid, semi-solid, or gel-like translucent material that is defined by relative translation of laser 20 to the material.

Substrate 10 has a coating of one or more active or functional biomolecules 12 applied thereon, as shown in FIG. 1B. Biomolecules are any biologically active molecules or molecules that modify a function or an activity of a biological or biochemical entity. One or more biomolecules 12 are biomolecules that are attachable to a substrate and can be ablated by laser exposure. One or more biomolecules 12 may be any biomolecule that can be attached, covalently or noncovalently to a substrate. One or more biomolecules can be attached directly to the substrate or via a molecular or polymeric tether. One or more biomolecules 12, for example, may include proteins; extracellular matrix proteins such as fibronectin, vitronectin and collagen; soluble proteins such as growth factors, including vascular endothelial growth factor (VEGF), brain-derived neurotrophic factor (BDNF) or neuronal growth factor (NGF); proteins that are part of a cellular membrane, such as semaphorins, neuropilins, PAR1 receptor, ephrins or plexins; proteins that are intracellular; a coupling biomolecule that links a protein or other biomolecule to a substrate such as streptavidin or antibodies; blocking agents to provide space for coupling biomolecules, proteins or other biomolecules to bind to a substrate; antibodies; receptors; ligands; lipids; antigens; full-size proteins; protein domains; peptides; enzymes and/or enzyme substrates; polysaccharides; DNA, RNA, or other nucleic acids; small biomolecules such as nucleotides (e.g. cyclic adenosine monophosphate); fluorescent reporters, small molecules and drugs, peptides and enzymatic substrates; small molecules that bind covalently to proteins, peptides or nucleic acids; aggregates of biomolecules, small particles or colloids less than 10 µm, less than 5 µm, less than 1 µm, less than 500 nm, less than 200 nm, less than 100 nm, or less than 50 nm diameter, including quantum dots, superparamagnetic nanoparticles, quantum dots coated with biomolecules as described above, superparamagnetic nanoparticles coated with biomolecules as described above, dendrimers coated with biomolecules as described above, glass or silica particles coated with biomolecules as described above, liposomes coated with biomolecules as described above, viruses or phage particles and analogous particles; or any combination thereof.

The coating of one or more biomolecules 12 may be by any one of many conventional methods. The coated biomolecule may be covalently bound, or non-covalently bound. Covalent chemistries may include coupling compounds of the general structure X—R—Y, where X contains at least one reactive group that covalently binds to the substrate and Y contains at least one reactive group that covalently binds to the biomolecule, and R is a spacer group of varying length that does not react with either substrate or biomolecule. Examples of X and Y include components such as silanols, silanes, thiols, esters, gluteraldehyde, NHS-ester, DSP, other thiol-terminated compounds, cysteine residues, carboxylate treated with carbodiimide, and any combination thereof. Non covalent chemistries include adsorption to properly modified glass or other substrate, where the attachment of the molecule may be mediated by electrostatic forces, van der Waals forces, hydrophobic interactions, physical trapping, capillary forces, entropic forces and interactions, steric interactions, and any combination thereof.

One or more molecules 12 coated on substrate 10 may be have a thickness 13 of about 1 nm to about 20 nm. Thickness 13 of one or more biomolecules 12 may be a layer that is on average more than about 0 nm thick and less than about 50 µm, less than about 10 µm, less than about 5 µm, less than about 1 µm, less than about 500 nm, less than about 200 nm, less than about 100 nm, less than about 50 nm, less than about 20 nm, less than about 10 nm, less than about 5 nm, or less than about 1 nm thick. One or more molecules 12 coated on substrate 10 can be uniform or non-uniform. A non-uniform coating may be a coating including one or more biomolecules that are patterned, for example, by the method described herein or another method of patterning on substrate 10.

One example of substrate 10 coated with one or more biomolecules 12 includes coating fibronectin on glass coverslip substrates of dimensions 22 mm×22 mm. The coverslip substrates are plasma cleaned for approximately 5 minutes with a plasma cleaner (Harrick Plasma, Ithaca, N.Y.). The coverslip substrates are then cleaned for about 20 minutes in pirahna-solution, $H_2O_2$:$H_2SO_4$ (1:3 v/v). The coverslip substrates are then washed in water. The coverslip substrates are incubated in an ethanolic 3-aminopropyltriethoxysilane (APTES); Gelest, Inc., Morrisville, solution, ethanol 99.5%/APTES 99+%, 10:1 v/v solution, in 1 milliMolar (mM) acetic acid for 3 hours, rinsed in water, then dried overnight in a dry-box having approximately <25% relative humidity or baked at 110° C. for about 2 to about 3 hours. Approximately 200 microliters (µL) of human fibronectin (Invitrogen, Carlsbad, Calif.) in phosphate buffered saline (PBS) is pipetted onto the coverslip substrates. The coverslip substrates are incubated at 4° C. for about 12 to about 16 hours and then at 37° C. for about 2 hours. The coverslip substrates are then rinsed in water and dried under nitrogen gas. The coverslip substrates are stored in a drybox and may be used within three weeks although the fibronectin retains functions for at least several months.

A laser 20 is applied to the coating of one or more biomolecules 12, as shown in FIG. 1C. Laser 20 may include a laser system having a focusing lens system 22, a mirror 24, and/or shutter system 26. Laser 20 applies a dose of electromagnetic radiation sufficient to cause a predetermined level of ablation on substrate 10. The amount of laser radiation delivered to the biomolecules on the surface can be described by the applied dose of the laser. There are two components to the dose of the laser—the intensity of the laser on the biomolecules and the total time the biomolecules are exposed to the laser. The intensity, also called power density and irradiance, of the laser is the amount of energy per unit time per unit area the laser delivers to the substrate. The intensity depends on the optical system of the laser and the output power of the laser. The output power of the laser is the amount of energy the laser outputs per unit time. The fluence of the laser is a product of the irradiance of the laser and the exposure time and is the total amount of energy delivered by the laser to an area. The amount of ablation depends on the dose: the greater the laser intensity or fluence on the substrate, the greater the applied dose, and the greater amount of biomolecule ablation. Typically the area receiving the applied dose and which is used to determine the intensity or fluence is defined by the diameter of the intersection of laser focal volume 14 with the surface of substrate 10. This area is typically called the laser spot. For example, if the laser is focused onto a glass coverslip, the area used to determine the dose is that of the laser spot on the coverslip—that is the intersection of the focal volume at its narrowest with the surface of the coverslip.

Laser 20 may be focused as to increase intensity and decrease size of a laser focal volume 14 that is applied to substrate 10. A diameter of laser 20 at laser focal volume 14 that interacts with one or more biomolecules 12 on substrate 10 may be as small as diffraction limited and as large as permitted by available power to achieve ablation. Laser 20 may deliver the laser radiation to substrate 10 by a near-field source, for example, an optical fiber with an aperture at a front end with a diameter smaller than a wavelength of light, positioned within one wavelength of substrate 10 that produces an irradiated area smaller than a diffraction-limited spot.

Laser 20 may be of any wavelength or combination of wavelengths that can ablate function or activity of one or more biomolecules, such as wavelengths between about 190 nm and about 11 μm. Laser 20 can be pulsed or continuous wave. The pulses can be of any length and number that is sufficient, given other laser parameters including power and focus, to achieve ablation, such as pulses of about $1\times10^{-15}$ seconds to about $1\times10^{2}$ seconds.

Laser 20 may be written over a substrate 10 by scanning laser 20, for example, as shown in FIG. 1D, and/or translating a stage holding substrate 10 in all three axes with respect to an optical axis of laser 20. Substrate 10 may be rotated in all three axes with respect to an optical axis of laser 20. Laser 20 translates a position of the laser radiation on substrate 10. Laser 20 may translate the position of the laser radiation by shutter 22 and/or a mirror 24.

Writing laser 20 over substrate 10 is a serial process. A computer may control scanning laser 20 and/or translating the stage holding substrate 10 and/or a shutter 22 that prevents or allows the application of laser 20 to one or more biomolecules 12 on substrate 10. One or more operator-defined predetermined patterns and/or laser parameters may be programmed into the computer. The computer is described herein by way of example as control processing unit. Of course, it is contemplated by the present disclosure for the computer to include any programmable circuit, such as, computers, processors, microcontrollers, microcomputers, programmable logic controllers, application specific integrated circuits, and other programmable circuits. It is further contemplated by the present disclosure that the computer is any number of control devices providing various types of control, e.g., centralized, distributed, redundant and/or remote control.

Production of arbitrary patterns on substrate 10, as shown in FIGS. 1E and 1F, is possible by writing laser 20 over substrate 10. An arbitrary pattern includes of a non-ablated portion 17 that includes one or more biomolecules 12 of at least one functional and/or active biomolecule and an ablated portion 15 of at least one wholly or partially ablated biomolecule distributed in any fashion on substrate 10. Ablated portion 15 is any region that can be physically realized by translation or rotation of the laser radiation relative to substrate 10 or translation and rotation of substrate 10 relative to the laser radiation, in one, two, or three dimensions. An arbitrary pattern includes points, lines, polygons, smooth irregular shapes, and regular or irregular volumes.

A range of function and activity of ablated biomolecules within ablated portion 15 of the arbitrary pattern can be from 100% functional and 100% active to 0% functional and 0% active. The arbitrary pattern may include a complete and whole biomolecule, a fraction of the biomolecule, or a complete absence of the biomolecule, or any combinations thereof. The dimensions of features of active or functional biomolecules in the arbitrary pattern are as small as less than about 1 nm and as large as 1 meter or as large as permitted by a translation system that changes the relative position of the substrate 10 to that of laser 20. Shapes of features of the arbitrary pattern are limited by dimensions of the focused laser spot on substrate 10 that ablates one or more biomolecules 12 that form ablated portion 15. Feature dimensions may be achieved by approaching a center of a feature of the pattern from two or more sides with laser radiation, ablating each side until as few as one functional or one active molecule remains in the feature. The one or more ablated portions having at least one dimension in the plane of the substrate from at least 0.1 nanometer, at least 1 nanometer, at least 10 nanometers, at least 100 nanometers, or at least 250 nanometers to 1 meter. One or more non-ablated portions is on the substrate. The one or more non-ablated portions having at least one dimension in the plane of the substrate from about at least 0.1 nanometer, at least 1 nanometer, at least 10 nanometers, at least 100 nanometers, or at least 250 nanometers to 1 meter. The ablated portions have less than 100% of biological function or activity, or biochemical function or activity of the one or more biomolecules on the substrate.

Gradient patterns of one or more biomolecules 12 on substrate 10 may be created by laser 20. A gradient pattern is an arbitrary pattern in which an extent of activity or function per unit distance, area, or volume, and any combination thereof varies with position on a substrate uniformly coated substrates. Multiple independent operational parameters determine the extent of a gradient, and because writing with laser 20 is a serial process, operational parameters can be varied continuously during writing to generate gradients over length scales from least 0.1 nanometer, at least 1 nanometer, at least 10 nanometers, at least 100 nanometers, or at least 250 nanometers to 1 meter. Operational parameters include an optical system, a wavelength of a laser, a pulse rate and a pulse duration (if pulsed) of a laser, an output power of a laser, a laser intensity, a laser fluence, an energy density at a the focus, a scan or translation speed of a substrate relative to a laser focus, a mode of a laser, a size and beam quality ($M^2$) of a focused laser spot.

One or more biomolecules 12 have a portion that is ablated with laser 20 in the predetermined pattern. Ablation includes inactivation of biomolecules or biological functionality or destruction or removal of biomolecules. The predetermined pattern of one or more biomolecules 12 includes an ablated portion 15 and a non-ablated portion 17 that includes one or more biomolecules 12. Ablated portion 15 includes fully or partially inactive or non-functional biomolecules or fully or partially destroyed biomolecules or includes no biomolecules (they have been removed) and non-ablated portion 17 includes active and functional biomolecules.

Ablated portion 15 and non-ablated portion 17 can be of uniform or non-uniform height. In contrast to applying biomolecules in a pattern on a substrate, ablating ablated portion 15 of one or more biomolecules 12 forms the predetermined pattern by removing or inactivating the portion of one or more biomolecules 12. The predetermined pattern can be either positive, in which non-ablated portion 17 contains one or more of biomolecules 12, or negative. A negative predetermined pattern ablates an ablated portion and backfills the ablated portion with one or more biomolecules. Any biomolecules may backfill the ablated portion including biomolecules that are the same as or different than the one or more biomolecules in non-ablated portions.

Figure 5:
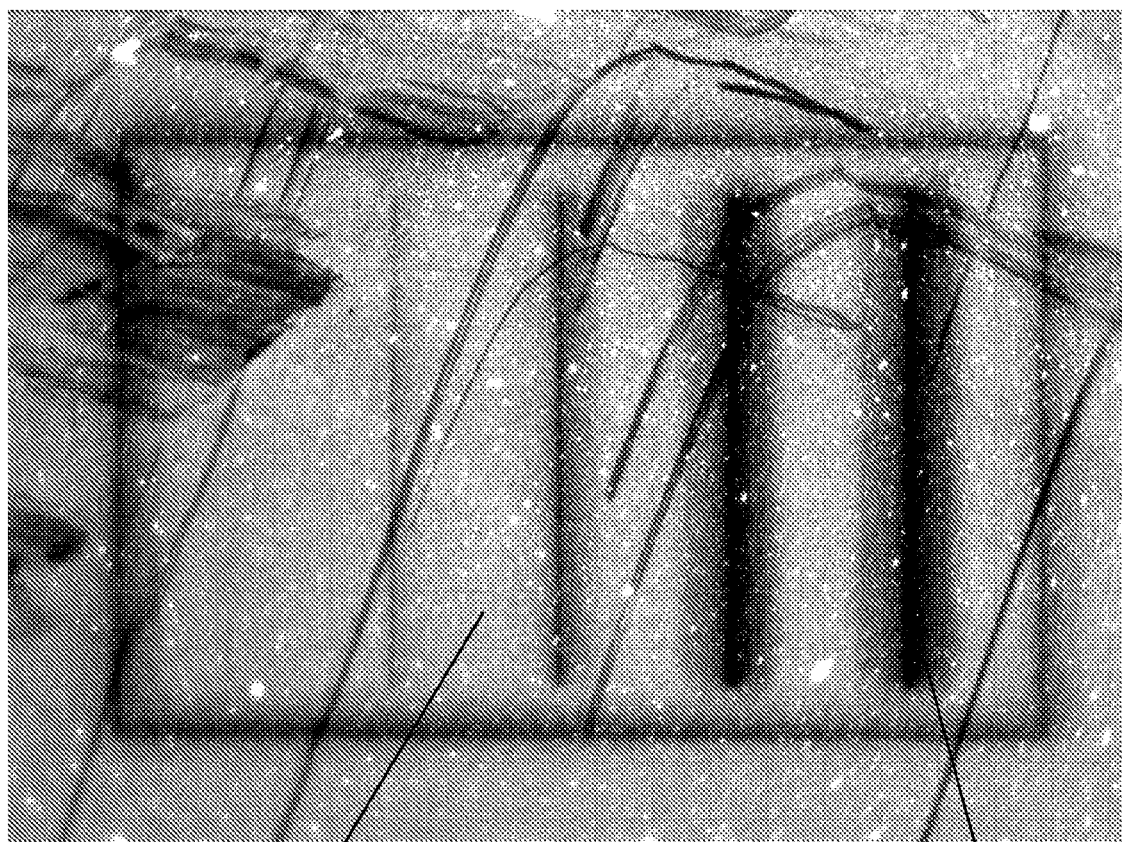
FIG. 5 is an immunofluorescence image of a surface coated with surface bound fibronectin, where the fibronectin is stained with an antibody against fibronectin, in a pattern formed by different doses of a laser in accordance with the present disclosure showing dose dependence of inactivation of surface bound fibronectin with the dose increasing from left to right, and where biomolecules on the substrate were submerged in an aqueous solution when ablation was performed, and the fluorescence intensity of the fibronectin staining is proportional to the activity of the fibronectin; thus, the fibronectin activity in the pattern ranges from high (light areas) to low (dark areas), and the irregular dark lines and shapes are the result of abrasion of the sample post laser exposure.

Coating substrate 10 with one or more biomolecules 12 is independent of ablating ablated portion 15 of one or more biomolecules 12 with laser 20 in the predetermined pattern, so that the coating and the predetermined pattern may be formed in a wide range of environments. The environment for coating the substrate 10 with a one or more biomolecules 12 and the environment for ablating the predetermined pattern with laser irradiation can be different environments. The range of environments for ablation may include biomolecules that are dry in an ambient atmosphere; dry in a selected gas that may influence the patterning process; biomolecules that are covered by a thin layer of liquid; biomolecules that are hydrated by a humid environment; biomolecules that are hydrated by an aqueous environment; biomolecules that are maintained in a non-aqueous environment; biomolecules that are maintained in a aqueous environment; and/or biomolecules that are in a vacuum. Substrate 10 may be submerged in water for ablating ablated portion 15 of one or more biomolecules 12 with laser 20. For example, FIG. 5 shows a pattern of regions of ablated fibronectin 85 and regions of non-ablated fironectin 82 on a substrate in water. FIG. 5 includes irregular streaks across the surface as a result from inadvertent mechanical abrasion subsequent to patterning.

Ablation can occur within or in proximity to a focal volume 14 of laser beam 21, and can result from photochemical, photothermal, or photophysical interactions or combinations of the three classes of interactions of the laser radiation with a biomolecule, a substrate, a coupling agent, or combinations of thereof. Photochemical effects include electronic excitation and subsequent bond breaking of specific chemical bonds within the substrate, the biomolecule, or coupling agent. Photothermal effects include heating of the biomolecule, substrate, or coupling agent by laser 20, and subsequent thermal response to a change in local temperature. For example, a biomolecule may undergo a change of conformation at increased temperature or at least one bond within that biomolecule may break. Photophysical effects include interactions, for example in an electrostatic or ballistic manner, of any removed material with the biomolecules, substrate, or coupling agent. Photophysical also includes interactions of a laser-generated plasma with the biomolecules, substrate, or coupling agent.

A degree of ablation varies with, wavelength of the laser, optical properties of the substrate and biomolecule, absorptive properties of the substrate and biomolecule, and thermal properties of the substrate and biomolecule, the species of biomolecule, and the optical, absorptive, and thermal properties of the coupling molecules. Exposure time of substrate 10 to focal volume 14 of laser beam 21 can range from the duration of a single pulse (1 femtosecond at the current state of the art) to seconds. Laser intensity can range from 0 Joules/centimeter$^2$ (J/cm$^2$) to the maximum provided by the current state of the art. The practical upper bound will be no greater than the intensity that can damage substrate 10. For example, for a glass substrate and a PALM laser described herein, the upper bound is approximately 200 microJoules/pulse. Laser wavelengths can range from deep UV (<200 nm) to far infra red (>10 µm). Substrate optical properties can range from opaque to transparent to a specific laser wavelength. Substrates can be reflective. Laser 20 may have an intensity that forms a microplasma that causes ablation upon contact of the microplasma with one or more biomolecules 12. Laser 20 may have a wavelength that excites one or more bonds within one or more biomolecules 12 and thereby causes ablation therein. Laser 20 may transfer heat or irradiate one or more biomolecules 12 or substrate 10, thereby causing ablation.

The predetermined pattern including one or more ablated portions 15 and one or more non-ablated portions 17 may be used for controlling cell shape or function of fibroblasts 116. For example, FIG. 1F shows an illustrative fluorescence micrograph of fibroblasts 116 attached to a patterned fibronectin 112 coated surface including ablated fibronectin 115 and functional fibronectin 117 that includes fibronectin 112. The predetermined pattern including one or more ablated portions 15 and one or more non-ablated portions 17 may be used to study or control neuronal guidance; to study or control cellular migration; to study or control cell division; to study or control and other biological processes; to study or control engineered tissue constructs including vascular constructs; to study or control functional properties of cells including secretion of important proteins (e.g. insulin); to study or control mechanical properties including elastic modulus and adhesive force; to study or control intra- and inter-cellular signaling; to make in vitro diagnostic assays including microarrays; or any combination thereof.

In one example of patterning a Zeiss PALM microbeam laser dissection microscope with a 337.1 nanometer wavelength pulsed laser with pulses of less than 4 nanoseconds (ns) and of 300 microjoules/pulse at a 30 Hertz (Hz) repetition rate, with a motorized stage, and with the PALM ROBO software was used. A predetermined pattern was drawn using the PALM ROBO software. Parameters such as laser energy, write speed, and UV focus were selected to optimize the predetermined pattern or portion of a pattern. Optimized operating parameters included a UV energy of 60%, a cut speed of 10 µm/s, and a UV focus value of 49. The accessible range for the UV energy parameter was between 0% and 100%. The accessible range for the cut speed was between 0 µm/s and 70 µm/s. The accessible range for the UV focus value was between 0 and 100. A 40×, 1.4 NA objective was used to focus the laser energy onto the substrates. The laser energy value is proportional to the intensity of the laser, and it is proportional to the applied does of the laser on the substrate.

Figure 6A:
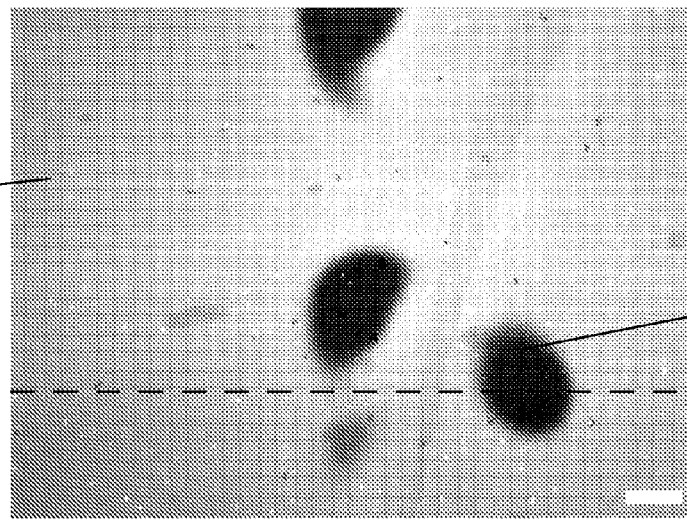
FIG. 6A is an immunofluorescence image of a surface coated with surface bound fibronectin, where the fibronectin is stained with an antibody against fibronectin, in a pattern formed by point exposures of a $CO_2$ laser with a wavelength of 10.6 μm, and the scale bar represents 35 micrometers, and the fluorescence intensity of the fibronectin staining is proportional to the activity of the fibronectin; thus, the fibronectin activity in the pattern ranges from high (light areas) to low (dark areas)
Figure 6B:
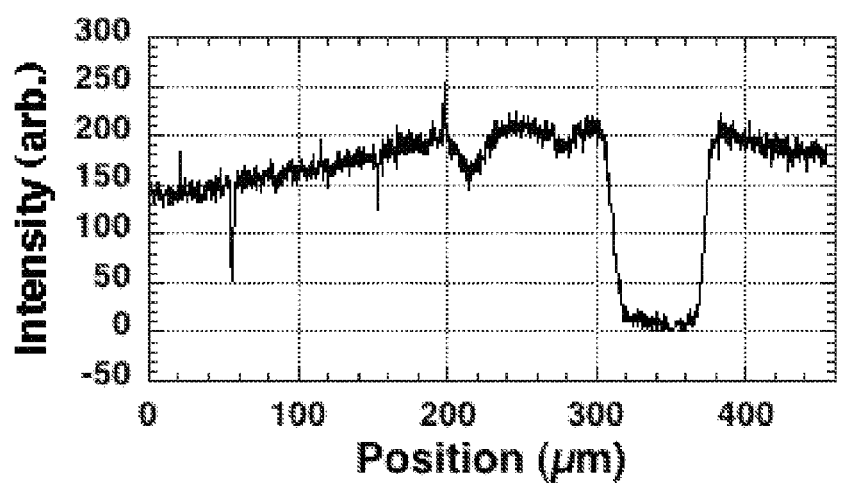
FIG. 6B is a graph showing a plot of fluorescence intensity as a function of position from left to right within the dashed line in FIG. 6A.

FIG. 6A is an immunofluorescence image of a surface coated with surface bound fibronectin 92, where fibronectin 92 is stained with an antibody against fibronectin, and a pattern of regions of ablated fibronectin 95 was formed by point exposures of a $CO_2$ laser with a wavelength of 10.6 μm, and the fluorescence intensity of the fibronectin staining is proportional to the activity of the fibronectin. The fibronectin activity in the pattern ranges from high (light areas) to low (dark areas). FIG. 6B is a graph showing a plot of fluorescence intensity as a function of position from left to right within the dashed line in FIG. 6A.

Figure 7A:
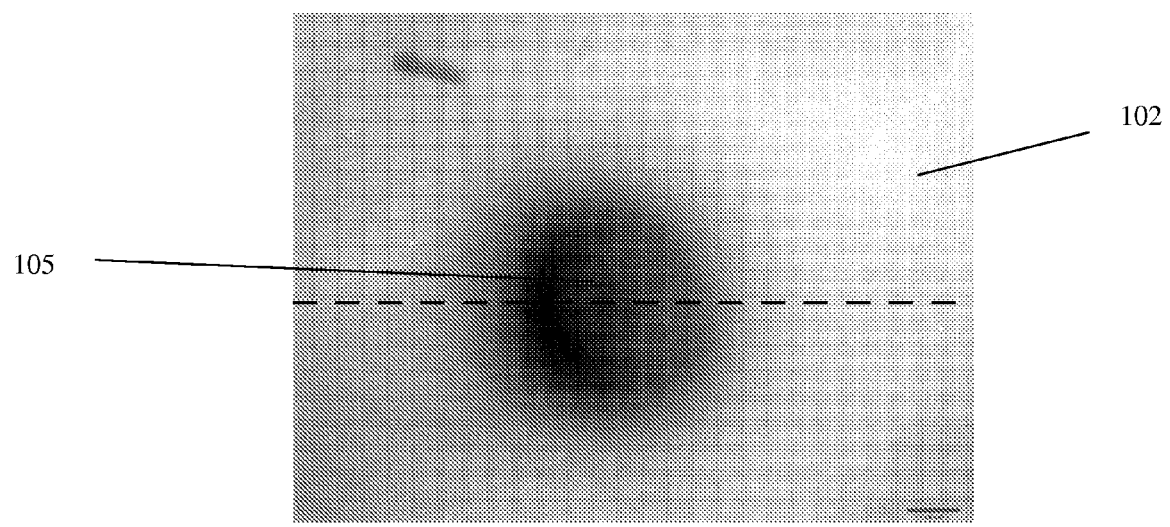
FIG. 7A is an immunofluorescence image of a surface coated with surface bound fibronectin, where the fibronectin is stained with an antibody against fibronectin, in a pattern formed by a single point exposure of a YAG (yttrium aluminium garnet) laser with a wavelength of 1064 nanometers, and the scale bar represents 35 micrometers, and the fluorescence intensity of the fibronectin staining is proportional to the activity of the fibronectin; thus, the fibronectin activity in the pattern ranges from high (light areas) to low (dark areas)
Figure 7B:
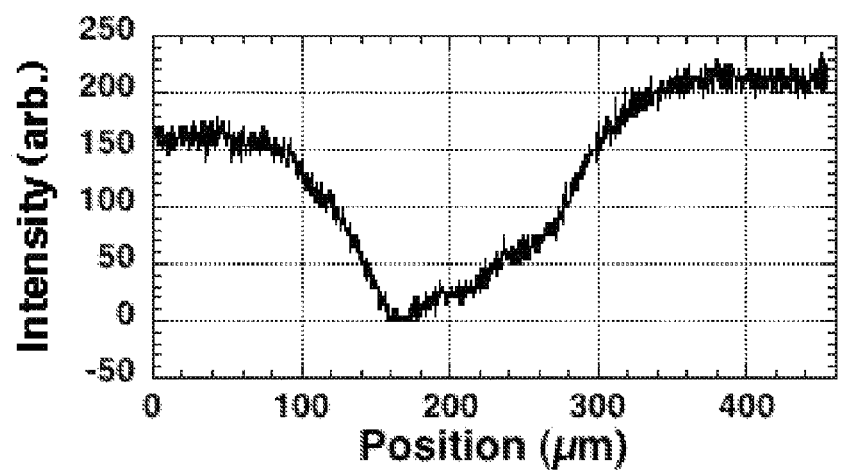
FIG. 7B is a graph showing a plot of fluorescence intensity as a function of position from left to right within the dashed line in FIG. 7A.

FIG. 7A is an immunofluorescence image of a surface coated with surface bound fibronectin 102, where fibronectin 102 is stained with an antibody against fibronectin, in a pattern 105 formed by a single point exposure of a YAG laser with a wavelength of 1064 nanometers, and the fluorescence intensity of the fibronectin staining is proportional to the activity of the fibronectin. The fibronectin activity in the pattern ranges from high (light areas) to low (dark areas). FIG. 7B is a graph showing a plot of fluorescence intensity as a function of position from left to right within the dashed line in FIG. 7A.

Figure 3A:
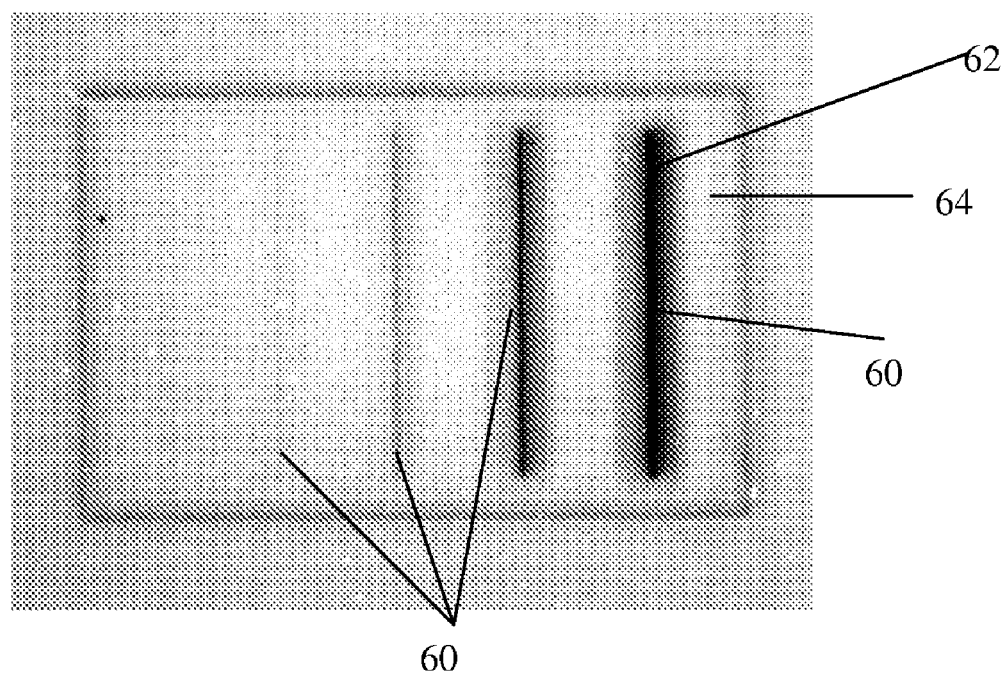
FIG. 3A is an immunofluorescence image of a surface coated with surface bound fibronectin, where the fibronectin is stained with an antibody against fibronectin in a pattern formed by different doses of a laser in accordance with the present disclosure showing dose dependence of inactivation of surface bound fibronectin with the dose of the laser increasing from left to right, and the fluorescence intensity of the fibronectin staining is proportional to the activity of the fibronectin; thus, the fibronectin activity in the pattern ranges from high (light areas) to low (dark areas), the image is 225 micrometers wide.

FIG. 3A illustrates an immunofluorescence image of a surface coated with surface bound fibronectin, where the fibronectin is stained with an antibody against fibronectin. A pattern including a series of vertical lines 60 was formed by different doses of a laser shows dose dependence of inactivation of surface bound fibronectin with the dose increasing from left to right. Each line of vertical lines 60 was exposed to a different laser intensity with laser intensity increasing from left to right in FIG. 3A. The laser intensity is proportional to the UV energy parameter of the Zeiss PALM laser system.

Figure 3B:
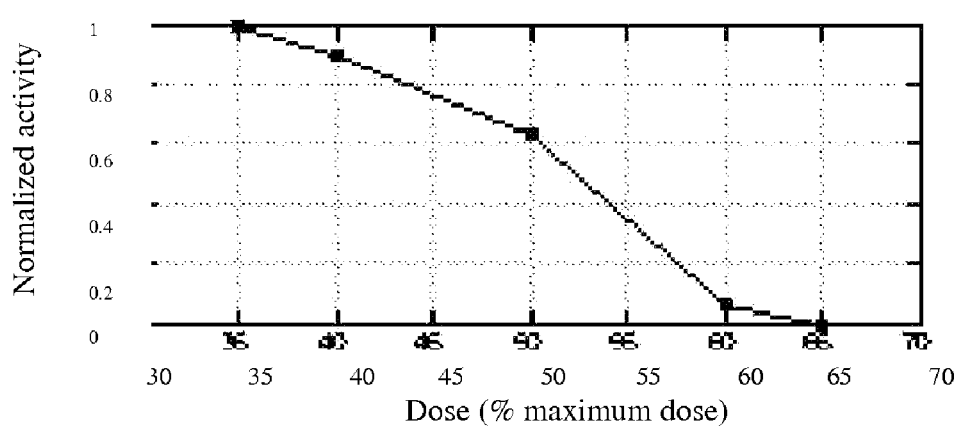
FIG. 3B is a graph showing normalized fibronectin activity, as measured by the fluorescence resulting from the antibody against fibronectin as a function of applied laser dose, on the surface of FIG. 3A.

Functional activity of the fibronectin in exposed regions 62 and unexposed regions 64 was quantified by immunofluorescence and fluorescence microscopy. The fluorescence intensity is presumed to be proportional to fibronectin activity. As shown in FIG. 3B, normalized fibronectin activity, measured by immunofluorescence resulting from the antibody against fibronectin, varies as a function of dose of the surface of FIG. 3A; thus, the laser inactivates substrate-attached protein in a dose-dependent manner. At low laser intensities, for example, 50% laser intensity, the plasma inactivates a fraction of the total protein activity on the substrate and at greater intensities, for example, greater than 60% laser intensity, there is greater or total inactivation of protein activity, as shown in FIG. 3B. Intensities greater than 70%, for example, may damage the coverslip. At sufficiently high intensities, the plasma removes biomolecules from the substrate as well as inactivates the biomolecules.

Figure 4A:
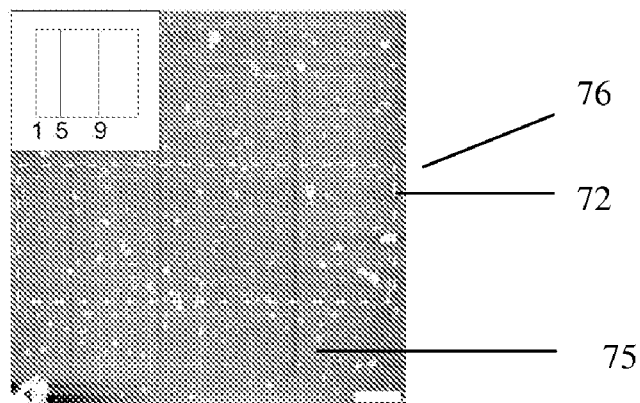
FIG. 4A is an atomic force microscope topographic image of a surface coated with surface bound fibronectin, having a pattern in which the vertical lines have been exposed to the laser one, five, and nine times as illustrated in the inset, the image is 90 micrometers wide.
Figure 4B:
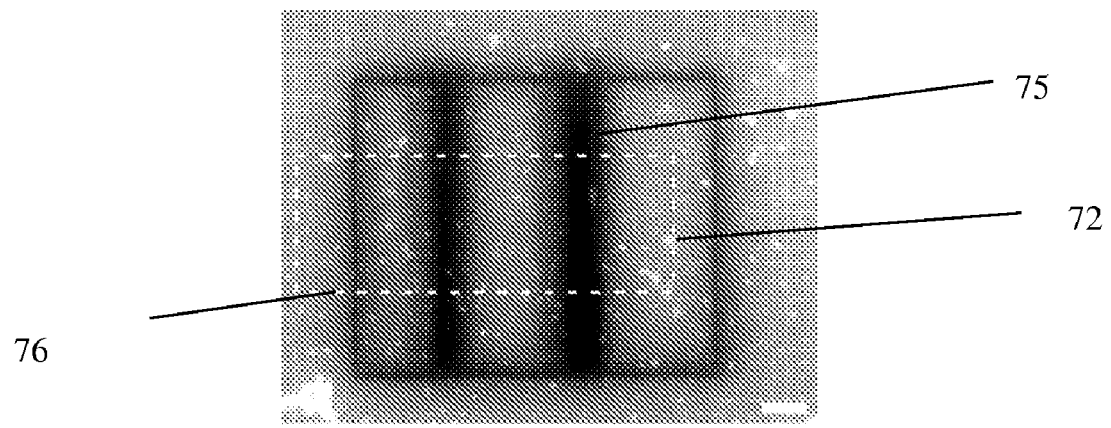
FIG. 4B is an immunofluorescence image of the image of FIG. 4A, where following a topographic imaging for FIG. 4A, the fibronectin is stained with an antibody against fibronectin, and the fluorescence intensity of the fibronectin staining is proportional to the activity of the fibronectin; thus, the fibronectin activity in the pattern ranges from high (light areas) to low (dark areas), The image is 120 micrometers wide.
Figure 4C:
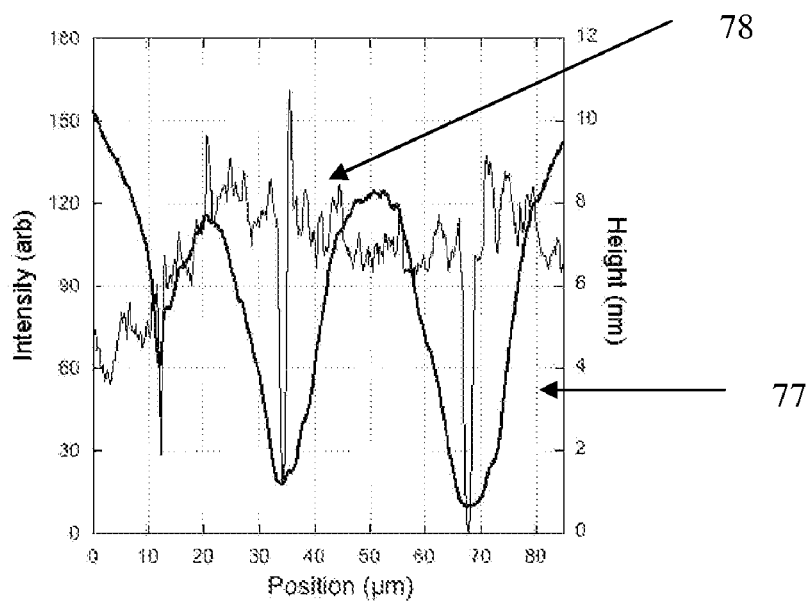
FIG. 4C is a graph showing a first plot of fluorescence intensity (thick line) as a function of position from left to right within a dotted box of FIG. 4B and showing a second plot (thin line) showing height from left to right within the dotted box of FIG. 4A showing profiles of atomic force microscope topograph (thin line) demonstrating that inactivation can be achieved without removal of mass that is measurable by the atomic force microscope.

Referring to FIGS. 4A through 4C, inactivation can be achieved without removal of mass that is measurable by an atomic force microscope. As shown in FIG. 4A, an atomic force microscope topographic image of a surface coated with surface bound fibronectin 72 has a pattern formed by ablated fibronectin 75. FIG. 4B shows an immunofluorescence image of FIG. 4A, where following the topographic imaging the fibronectin was stained with an antibody against fibronectin. FIG. 4C shows a first plot 77 of fluorescence intensity (thick line) as a function of position from left to right within a dotted box 76 of FIG. 4B. FIG. 4C shows a second plot 78 showing height from left to right within dotted box 76 of FIG. 4B of the atomic force microscope topograph (thin line).

Referring now to FIG. 2A, the method for ablating biomolecules on a substrate with a laser to form a predetermined pattern including one or more ablated portions and one or more non-ablated portions may include a tube 50 having a solvent 54 within a tube interior. Tube 50 is translucent, such as, for example, a glass capillary. The method for ablating biomolecules on a substrate with a laser to form a predetermined pattern including one or more ablated portions and one or more non-ablated portions may include coating one or more biomolecules 12 on an interior surface of a tube wall of tube 50 in solvent 54, as shown in FIG. 2B. Laser 20 irradiates through the tube wall to interior surface having one or more biomolecules 12 coated thereon, as shown in FIG. 2C. As shown by arrows 56 and 58 in FIGS. 2D and 2E, translating laser beam 21 with mirror 24, activating and deactivating laser beam 21 by shutter 26, rotating or translating tube 50, or any combinations thereof exposes areas of one or more of molecules 12 to laser beam 21. The radiation of laser beam 21 ablates one or more one or more biomolecules 12 forming one or more ablated portions 15 in a predetermined pattern, as shown in FIG. 2D. FIG. 2E shows culture adherent cells 57 on the interior surface of tube 50. Growth and function of culture adherent cells 57 are influenced by ablated portions 15 of the predetermined pattern of the one or more biomolecules 12.

The predetermined pattern on tube 50 can be use for a wide range of applications, including protein/nucleic acid biochip sensors, cell-based sensors, lab-on-a-chip assays, lab-in-a-capillary assays, cell adhesion assays, cell translocation/migration/invasion/chemotaxis assays, neuronal-guidance assays, tissue-engineering, biomedical device biocompatability, vasculature regeneration, control of cellular biological processes such as adhesion, migration, and division, control over functional properties of cells such as secretion, shape mechanics, and intra and intercellular signaling.

To establish laser operating parameters for using the method for ablating biomolecules on a substrate with a laser to form a predetermined pattern including one or more ablated portions and one or more non-ablated portions for patterning any particular biomolecule, the laser parameters that influence the ablation process can be examined. The amount of laser radiation delivered to the biomolecules on the surface can be described by the applied dose of the laser. There are two components to the dose of the laser—the intensity of the laser on the biomolecules and the total time the biomolecules are exposed to the laser. The intensity, also called power density and irradiance, of the laser is the amount of energy per unit time per unit area the laser delivers to the substrate. The intensity depends on the optical system of the laser and the output power of the laser. The output power of the laser is the amount of energy the laser outputs per unit time. The fluence of the laser is a product of the irradiance of the laser and the exposure time and is the total amount of energy delivered by the laser to an area.

Parameters for a continuous wave (CW) laser that contribute to the applied dose of a CW laser can include the laser wavelength, the laser output power, the exposure time, the spatial mode, and the size and quality of the focused laser spot on the substrate. The wavelength of the laser can be selected based on the known physical chemistry of the biomolecules being ablated, or wavelengths can be tested exhaustively by incrementing the wavelength 10 nm at a time from about 190 nm to 11 μm. For each wavelength range of intensities and doses can be examined. The intensities, for example, can be varied from 0 W/μm$^2$ to 5 W/μm$^2$ by adjusting the output power of the laser, and the exposure times can range from 1 μs to 1 s, resulting in a fluence that varies from 0 J/μm$^2$ to 5 J/μm$^2$. Each combination of parameters can be used to expose an area on substrate 10 coated with the biomolecule of interest, where this area is large enough for suitable analysis, for example by atomic force microscopy or immunofluorescence microscopy. The substrate then can be analyzed to determine the function or activity of the biomolecule or biomolecules in the irradiated area. The activity or function can be determined by for example enzymatic activity, fluorescence, antibody binding, ligand binding, cell binding, cell repulsion or any suitable functional assay for the biomolecule in question. Once the appropriate combination of parameters for ablation is established, these parameters can be used in method for ablating biomolecules on a substrate with a laser to form a predetermined pattern including one or more ablated portions and one or more non-ablated portions to pattern the biomolecule of interest.

Parameters for a pulsed laser that contribute to the applied dose of a pulsed laser can include the laser wavelength, the laser pulse width, the laser pulse frequency, the laser output peak power, the exposure time, the spatial mode, and the size and quality of the focused laser spot on the substrate. The wavelength of the laser can be selected based on the known physical chemistry of the biomolecules being ablated, or wavelengths can be tested exhaustively by incrementing the wavelength 10 nm at a time from about 190 nm to 11 μm. For each wavelength range of intensities and doses can be examined. Pulsed lasers in general have greater intensities than CW lasers due to the short pulse times (typically on the order of $10^{-9}$ s, $10^{-12}$ s, or $10^{-15}$ s for the current state of the art). The intensities, for example, can be varied from 0 W/μm² to 100 kW/μm² by adjusting the output power of the laser, and the exposure times can range from 1 μs to 1 s. Each combination of parameters can be used to expose an area on a substrate coated with the biomolecule of interest, where this area is large enough for suitable analysis for example by atomic force microscopy or immunofluorescence microscopy. The substrate then can be analyzed to determine the function or activity of the biomolecule or biomolecules in the irradiated area. The activity or function can be determined, by for example enzymatic activity, fluorescence, antibody binding, ligand binding, cell binding, cell repulsion or any suitable functional assay for the biomolecule in question. Once the appropriate combination of parameters for ablation is established, these parameters can be used in method for ablating biomolecules on a substrate with a laser to form a predetermined pattern including one or more ablated portions and one or more non-ablated portions to pattern the biomolecule of interest.

Many different types of lasers can be used for the method for ablating biomolecules on a substrate with a laser to form a predetermined pattern including one or more ablated portions and one or more non-ablated portions. To determine if a laser can be used, a test of relevant parameters can be carried out. For example, a pulsed 10 Watt YAG laser with a 50 kHz pulse frequency is tested by irradiating a substrate 10 coated with biomolecules 12. The laser is focused 14 onto the biomolecules. The substrate is exposed to the laser on points at different positions on the substrate for varying lengths of time, for example 1 μs, 10 μs, 100 μs, 1 ms, 10 ms, 100 ms and 1 s at a series of different output powers, for example, 0.5 W, 1 W, 5 W, ad 10 W. The substrate is then analyzed to determine the function or activity of the biomolecule or biomolecules in the irradiated area. The activity or function can be determined by for example enzymatic activity, fluorescence, antibody binding, ligand binding, cell binding, cell repulsion or any suitable functional assay for the biomolecule in question. Once the appropriate combination of parameters is established, these parameters can be used in method for ablating biomolecules on a substrate with a laser to form a predetermined pattern including one or more ablated portions and one or more non-ablated portions to pattern the biomolecule of interest. A similar approach can be used to determine the optimal parameters for a continuous wave laser system. The selection of lasers may also be guided by physical chemical properties of the biomolecules being patterned, by someone skilled in the art.

EXAMPLE 1

Cellular Migration

Method for ablating biomolecules on a substrate with a laser to form a predetermined pattern including one or more ablated portions and one or more non-ablated portions is used to study or control cellular migration. The secreted protein vascular endothelial growth factor (VEG-F) induces cell migration in vitro. Most experiments on this kind are performed using one or more point sources of diffusible VEG-F, and the migration of cells towards that source is observed over time. Although this system has produced substantial information about the biology and biochemistry of cell migration, this source-and-diffusion model of VEG-F is restricted to distributions of molecules that are achieved with combinations of sources of diffusible VEG-F, and it is exceedingly difficult to characterize in terms of the concentration gradients and the change of the gradients over time. The effects of complex gradients of VEG-F activity on endothelial cell function are studied using method for ablating biomolecules on a substrate with a laser to form a predetermined pattern including one or more ablated portions and one or more non-ablated portions in an aqueous environment. A bi-functional polyethyleneglycol (PEG) with one end functionalized with a silanol group and another end functionalized with an NHS-ester are used to coat a glass surface with VEG-F. The silanol moiety will bind covalently to the glass surface, and the NHS-ester will bind to amines in the VEG-F molecule. The PEG linker region ensures that the VEG-F is sufficiently free to diffuse in a small (typically 5-100 nm radius), but tethered volume in the aqueous solution. The gradient is time invariant at dimensions larger than the tether distance and are characterized, for example by immunofluorescence microscopy. The gradients produced are spatial distributions of VEG-F that are otherwise aphysical and that are not possible to produce by any physically realizable combination of sources of diffusible of VEG-F. A surface coated with VEG-F as described and patterned in solution using method for ablating biomolecules on a substrate with a laser to form a predetermined pattern including one or more ablated portions and one or more non-ablated portions are used to induce endothelial cells to migrate towards the regions on the substrate that have greater number of active VEG-F proteins. Complex patterns of active and inactive VEG-F are used to direct the migration of endothelial cells to specific regions on the substrate.

EXAMPLE 2

Gradient Pattern of a Growth Factor

To make a gradient pattern of a biomolecule on a substrate, the applied dose of the laser must be modulated as a function of position within the pattern. Modulating the dose can include maintaining a constant power density and varying the speed at which the substrate translates relative to the laser focus, maintaining a constant speed at which the substrate translates relative to the laser focus and varying the laser power density as a function of position.

A glass coverslip substrate is cleaned and coated with APTES. A biomolecule, such as the normally soluble growth factor VEGF, is attached to the coverslip using a tethering molecule such as a bifunctional polyethylene-glycol (PEG). The laser system is programmed to make a gradient pattern in which a rectangular area, for example, of the VEGF coated substrate is exposed to laser irradiation such that along one axis of the rectangle the applied dose of the laser irradiation is increased from a minimum to a maximum. This is accomplished by using a fixed laser intensity (532 nm wavelength, 0.2 W laser output focused with a 60×, 1.4 NA objective) and varying the speed at which the sample translates relative to the laser focus. The longer the focus remains on a single spot, the larger the applied dose of laser irradiation and the greater the ablation of the biomolecules exposed. Varying the speed from 0.001 µm/s to 100 µm/s will vary the applied dose by 5 orders of magnitude, and vary the ablation from a minimum (at 100 µm/s) to a maximum (at 0.001 µm/s). It is possible that the all biomolecules will be ablated at a dose below the maximum, and that there is a dose which ablates all biomolecules.

A second method to vary the dose it to keep constant the translation speed but vary the laser intensity as a function of laser focus position on the substrate.

EXAMPLE 3

Ablation in Solution

In this implementation, a glass coverslip is coated with fibronectin. An aqueous solution, PBS for example, is added to the coated surface of the coverslip, and the coverslip is placed on the stage of the laser system. The laser is focused to the surface of the coverslip coated with the fibronectin and that is in contact with the solution. The laser system parameters are set to inactivate the fibronectin, but not to remove it from the substrate and not to damage the coverslip (for example in the PALM system, laser power set to 55%, scan speed of 25 µm/sec, and a UV focus of 49), in a predefined pattern.

EXAMPLE 4

Neuronal Guidance

Method for ablating biomolecules on a substrate with a laser to form a predetermined pattern including one or more ablated portions and one or more non-ablated portions is used to study or control neuronal guidance. Biomolecules that guide neuronal cells during development, regeneration, wound healing and other processes include molecules from the molecular families of ephrins, semaphorins, slits, and netrins, and specific neuronal guidance molecules including brain-derived neurotrophic factor (BDNF) and neuronal growth factor (NGF). Neuronal growth guidance is attractive or inhibitory. For example, the semaphorins are a class of secreted and membrane bound molecules that guide the axonal growth cone. They are short-range inhibitory signaling molecules. For example, one difficulty with studying neuronal guidance in vitro with cell-membrane-bound semaphorins is that the spatial distribution of semaphorins on a layer of cells in a Petri dish, for example, is difficult to control. Method for ablating biomolecules on a substrate with a laser to form a predetermined pattern including one or more ablated portions and one or more non-ablated portions are used to control the spatial distribution of active and inactive semaphorins found in the cell membrane. A substrate that is coated with a specific semaphorin molecule from a cell membrane or the active binding domain of that molecule, and that is patterned using the method for ablating biomolecules on a substrate with a laser to form a predetermined pattern including one or more ablated portions and one or more non-ablated portions have regions of inactivated semaphorin molecules, regions of active semaphorin molecules, and if gradient patterning is used, regions composed of combinations of inactive and active semaphorins. Neurons plated and grown on such a substrate will move in a way that is influenced by the regions containing active semaphoring molecules and the regions containing inactive semaphoring molecules.

EXAMPLE 5

Cell Division

Method for ablating biomolecules on a substrate with a laser to form a predetermined pattern including one or more ablated portions and one or more non-ablated portions is used to study or control cell division. It has been shown using micro-contact printed patterns of extra cellular matrix proteins that the ECM geometry defines the axis of cell polarity (Thery et al., 2006) and guide the orientation of the cell division axis (Thery et al., 2005). ECM proteins such as fibronectin are attached to a substrate and patterned using method for ablating biomolecules on a substrate with a laser to form a predetermined pattern including one or more ablated portions and one or more non-ablated portions. Regions of active fibronectin that support the adhesion of a single or multiple cells are contemplated. The effect of the geometry of the ECM pattern on aspects of cell division such as the expression of specific genes, the timing of key events, the internal organization of organelles and other intracellular structures in the mother and daughter cells, the axis of cell division, the properties and dynamics of DNA replication, and the other phenomena that occur during mitosis, are examined and studied using standard cell biological techniques such as optical and fluorescent microscopy during each phase of mitosis. Processes related to cell division are also controlled. A HeLa cell, for example, plated on a 20 µm×60 µm rectangle of active fibronectin molecules surrounded by an expanse of inactive fibronectin has a high probability that its division axis will be parallel to the width of the rectangle. The effects of confinement to the rectangle on internal cellular structures such as the cytoskeleton are examined using optical or fluorescent microscopy while the cell is on the pattern. Other shapes and geometries are made as well with method for ablating biomolecules on a substrate with a laser to form a predetermined pattern including one or more ablated portions and one or more non-ablated portions for this purpose. Another embodiment of this example is to use substrates with a set of patterns, and then examine the combined effect of another factor or factors, such as soluble molecule or an environmental insult like a temperature change, on cell division.

EXAMPLE 6

Biological Processes

Method for ablating biomolecules on a substrate with a laser to form a predetermined pattern including one or more ablated portions and one or more non-ablated portions is used to study or control and other biological processes. The expression of genes within a cell is regulated by the interactions of a cell with a pattern of ECM proteins on a substrate (Chen et al., 1997; Dike et al., 1999). Patterns of ECM proteins, signaling molecules, growth factors, growth inhibitors, and other biomolecules are made using method for ablating biomolecules on a substrate with a laser to form a predetermined pattern including one or more ablated portions and one or more non-ablated portions to study or control biological processes such as gene expression, differentiation, metabolism, syntheses of proteins, degradation of proteins, secretion, ingestion, growth, apoptosis, spreading, rounding, inter and intracellular communication and signaling, regulation of cellular function, and others. For example, to study the effect of a pattern of epidermal growth factor (EGF) on DNA synthesis within Swiss 3T3 fibroblasts using the method for ablating biomolecules on a substrate with a laser to form a predetermined pattern including one or more ablated portions and one or more non-ablated portions, a surface is first be coated with EGF using a bifunctional PEG linker molecule as describe above. Then predefined patterns of inactive EGF and active EGF are made according to method for ablating biomolecules on a substrate with a laser to form a predetermined pattern including one or more ablated portions and one or more non-ablated portions, and the fibroblasts plated on the substrates and allowed to adhere, spread, and grow on the patterns. Assays to detect DNA synthesis (for example the percentage of nuclei labeled with 5-bromodeoxyuridine after 24 hours) are then be applied to the cells.

EXAMPLE 7

Engineered Tissue Constructs

Method for ablating biomolecules on a substrate with a laser to form a predetermined pattern including one or more ablated portions and one or more non-ablated portions is used to study, control engineered tissue constructs such as vascular constructs. Angiogenesis, the growth of blood capillaries, is regulated by soluble growth factors and insoluble extracellular matrix (ECM) molecules (Ingber, 1992). Vascular endothelial cells grown to confluence on a substrate with a uniform coating of ECM molecules do not have all the properties of a vasculature in vivo. A substrate patterned with ECM proteins using method for ablating biomolecules on a substrate with a laser to form a predetermined pattern including one or more ablated portions and one or more non-ablated portions in such a way as to introduce into onto the substrate a directional bias provide a more natural environment for the endothelial cells to grow, and thus result in a better model of vascular tissue for study or a better engineered substrate for large-scale production of engineered tissue. For example, parallel lines 5 μm wide of inactive fibronectin on a substrate of active fibronectin molecules cause the plated cells to orient themselves in the direction of the lines. If the cells are grown to confluence on such a pattern, even though the cells may grow over the inactive fibronectin, the two-dimensional tissue will have different mechanical properties in the direction parallel to the lines versus in the direction perpendicular to the lines, and will have mechanical properties that are more well-defined than those of layers of cells grown without control.

EXAMPLE 8

Functional Properties of Cells

Method for ablating biomolecules on a substrate with a laser to form a predetermined pattern including one or more ablated portions and one or more non-ablated portions is used to study or control functional properties of cells such as secretion of important compounds (e.g. insulin, triglycerides, steroids). It is known that the size of B-cells contributes to the insulin secretion, and that the environment and shape of mammary epithelial cells in vitro contributes to the secretion of triglycerides of milk fat. Substrates of ECM molecules such as fibronectin are patterned using method for ablating biomolecules on a substrate with a laser to form a predetermined pattern including one or more ablated portions and one or more non-ablated portions to identify and patterns of ECM protein that increase the secretion of these and other compounds from appropriate cell types (e.g. B-cells, epithelial cells, granulosa cells). To identify patterns of ECM proteins that increase secretion of insulin from B-cells, for example, a series of patterns are made using method for ablating biomolecules on a substrate with a laser to form a predetermined pattern including one or more ablated portions and one or more non-ablated portions that systematically vary in area, perimeter, geometry, and ECM protein. B-cells are plated and grown on substrates containing the patterns, and the levels of insulin secretion are measured. That pattern are optimized by examining a insulin secretion for a large number of highly distinctive shapes in the pattern, taking the shapes that produce the best insulin expression and varying the shapes in a narrower range of dimensions, and repeating this process until a pattern that promotes high levels of insulin express is identified. A pattern that is optimized for insulin secretion can then be determined and used for therapeutic, research, or diagnostic purposes.

EXAMPLE 9

Mechanical Properties of Cells

Method for ablating biomolecules on a substrate with a laser to form a predetermined pattern including one or more ablated portions and one or more non-ablated portions are used to study or control mechanical properties such as elastic modulus and adhesive force. It has been shown for ECM proteins patterned on substrates that the pattern geometry affects cytoskeletal protein organization (Berg et al., 2004) through interactions between the ECM proteins, the integrins, the focal adhesion complex, and other intercellular protein complexes. The cytoskeletal organization is the major contributor to cellular mechanics, which is quantified by, for example, the elastic modulus and the Poisson ratio. The mechanical properties of cells are important to their function. The adhesive force, for example, is a measure of the strength of adhesion between a cell and the substrate. Cells with a low adhesive force are easily removed from the surface under exposure to an applied flow, for example, but cells with a high adhesive force are not. Substrates with ECM proteins, for example fibronectin, patterned using method for ablating biomolecules on a substrate with a laser to form a predetermined pattern including one or more ablated portions and one or more non-ablated portions to include regions of active and inactive fibronectin of specific geometries that are used to modulate the cytoskeletal organization of cells plated on those patterns, and thus modulate the mechanical properties of the cells. Such patterns used in conjunction with assays for the mechanical properties of cells and/or the intercellular and intracellular signaling pathways that regulate the mechanical properties of cells elucidate the mechanisms by which the environment controls cellular mechanics. Such patterns can be used to control cellular mechanics for purposes such as tissue engineering, assay development, and biomedical research.

EXAMPLE 10

Intra- and Inter-Cellular Signaling

Method for ablating biomolecules on a substrate with a laser to form a predetermined pattern including one or more ablated portions and one or more non-ablated portions is used to study or control intra- and inter-cellular signaling. Controlling various cell functions and properties through the use of substrates patterned using method for ablating biomolecules on a substrate with a laser form a predetermined pattern including one or more ablated portions and one or more non-ablated portions. In order for the cells to respond to the patterns, there must be a signal delivered from the cell surface to the interior of the cell, often to the nucleus and the proteins and biomolecular complexes that regulate gene transcription. Thus in combination with assays to identify and characterize specific components of a signaling pathway or cascade within a cell or a collection of cells, patterns of biomolecules such as ECM proteins, growth factors, growth inhibitors, and cytokines, the pathways that cells use to react to their environment are investigated. For example, to determine the effect of patterns of epidermal growth factor (EGF) on the activity of the S6 kinase, patterns of active and inactive EGF on substrates are made using method for ablating biomolecules on a substrate with a laser to form a predetermined pattern including one or more ablated portions and one or more non-ablated portions. Cells plated on those patterns bind to the substrate attached EGF through EGF-receptor proteins on the cell surface. This binding induces a signal cascade that eventually includes activation of the S6 kinase. Assays for the S6 kinase activity are applied to these cells and the influence of EGF pattern shape on S6 kinase activity is measured. Cells in contact with other cells, such as those in a tissue or those grown to confluence in vitro, signal to each other by secretion of signaling molecules, direct contacts like gap junction channels, and mechanical linkages through stress fibers. The effect of the spatial distribution of biomolecules on the substrates of these collections of cells are examined and exploited using method for ablating biomolecules on a substrate with a laser to form a predetermined pattern including one or more ablated portions and one or more non-ablated portions. For example, method for ablating biomolecules on a substrate with a laser to form a predetermined pattern including one or more ablated portions and one or more non-ablated portions is used to make large islands of ECM protein like fibronectin onto which a number of cells are plated and grown to confluence on that island. Assays for inter and intra cellular signaling are applied to cells on the islands to determine the effect of, for example, island size, number of neighbors, mechanical properties of the collection of cells, on cell signaling pathways.

EXAMPLE 11

In Vitro Diagnostic Assays

Method for ablating biomolecules on a substrate with a laser to form a predetermined pattern including one or more ablated portions and one or more non-ablated portions is used to make in vitro diagnostic assays, including microarrays or cell arrays. In vitro diagnostic assays, in vitro high throughput, and in vitro high content screening assays, including those based on cellular responses to drugs, toxins, pathogens, therapeutic agents, biological and biochemical compounds, and the like, often require the identification and analysis of cells grown in vitro. Typically, such cells are randomly positioned over the substrate, and identifying and analyzing cells is a time consuming and expensive activity. Human expertise or automated image processing and analysis algorithms are used to identify and analyze cells in micrographs of the substrates. Patterns of ECM proteins such as fibronectin that include a shape defined geometry, for example a solid circle, 50 µm in diameter, of fibronectin, that is repeated many times over an area of a substrate such that each circle was in a predetermined location, for example a rectangular array of 100 µm pitch in each direction of solid fibronectin circles, reduce the time required to identify and analyze cells in the assay. The collection of micrographs, the identification of cells, and the analysis of the cellular response to the analyte(s) are faster because the cells are positioned in pre-defined locations. The repeated shapes are further optimized for the particular response. For example, an assay that screens for compounds that affect the expression of a particular gene in a specific cell line are based on repeated patterns of ECM protein that have been identified to optimize the expression of that gene in cells plated on those patterns. Compounds that inhibit or enhance the gene expression are then applied at different concentrations to substrates with cells plated on the patterns, the gene expression measured and correlated to the compound and the concentration.

EXAMPLE 12

Interior Surfaces

Another application of method for ablating biomolecules on a substrate with a laser to form a predetermined pattern including one or more ablated portions and one or more non-ablated portions include one or more of biomolecules 12 coated on an interior surface of a glass capillary or a translucent tube of a biopolymer, applying laser 20 to an exterior surface opposite the interior surface of the glass capillary, and ablating a one or more of biomolecules 12 in a predetermined patterned on the interior surface of the glass capillary. The predetermined pattern is used for a wide range of applications, including microfludic devices, protein/nucleic acid biochip sensors, cell-based sensors, lab-on-a-chip assays, lab-in-a-capillary assays, cell adhesion assays, cell translocation/migration/invasion/chemotaxis assays, neuronal-guidance assays, tissue-engineering, biomedical device biocompatability, vasculature regeneration, control of cellular biological processes such as adhesion, migration, and division, control over functional properties of cells such as secretion, shape mechanics, and intra and intercellular signaling.

EXAMPLE 13

Stem Cell Differentiation

Method for ablating biomolecules on a substrate with a laser to form a predetermined pattern including one or more ablated portions and one or more non-ablated portions are applied to substrates to study and control stem cell differentiation. Patterns of biomolecules on substrates control the differentiation of stem cells grown on the patterns. For example, adult rat hippocampal progenitor cells (AHPCs) plated on micropatterns of laminin preferentially acquired neuronal morphology compared to those AHPCs plated on unpatterned substrates (Recknor et al., 2006). The method for ablating biomolecules on a substrate with a laser to form a predetermined pattern including one or more ablated portions and one or more non-ablated portions is used, for example, to determine patterns of biomolecules that direct stem cells to differentiate into specific cell lines. For example, a set of patterns of active and inactive ECM molecules is made using method for ablating biomolecules on a substrate with a laser to form a predetermined pattern including one or more ablated portions and one or more non-ablated portions on a set of substrates such that each substrate has the same set of patterns but is coated with a different type biomolecule. Stem cells, human mesenchymal stem cells (hMSCs) for example, are plated and grown on each substrate in the set and monitored for differentiation to determine which ECM biomolecule and which pattern is most efficient for directing differentiation to a specific cell type, neurons for example. Another set of patterns are developed based on the results of the first pattern and biomolecule screen. For example, the dimensions of a particular class of shapes are varied systematically. hMSCs are plated on the new patterns of selected ECM biomolecules and monitored for differentiation. Repeated applications of this approach further refines the patterns to more efficiently and reliably direct stem cell differentiation.

EXAMPLE 14

Information

Method for ablating biomolecules on a substrate with a laser to form a predetermined pattern including one or more ablated portions and one or more non-ablated portions are used to study and control the amount of information in a pattern of biomolecules on a surface. The amount of information in a pattern is quantified using information theory (Shannon, 1948; Bell, 1948). Thus, the information in the spatial distribution of biomolecules patterned on a substrate using method for ablating biomolecules on a substrate with a laser to form a predetermined pattern including one or more ablated portions and one or more non-ablated portions are quantified, and such patterns are classified according to their information content. The response of cells plated on patterns with systematically varied amounts of information is examined and correlated to the information content of the patterns. For example, the morphology of cells varies with the information content of a pattern. Other cellular responses include gene expression, mitosis, differentiation, migration, secretion, apoptosis, inter- and intra-cellular signaling, metabolic responses, and mechanical responses.

EXAMPLE 15

Device Enhancement

Method for ablating biomolecules on a substrate with a laser to form a predetermined pattern including one or more ablated portions and one or more non-ablated portions are applied to enhance or to modify for new uses, including those described above, pre-existing devices including microscope coverslips, microscope slides, Petri dishes, cell culture flasks, multi-well plates, test tubes, eppendorf tubes, glass or plastic capillaries, sensor elements, biomedical implants, and gels.

EXAMPLE 16

Backfilling

A substrate, for example a glass coverslip, is plasma-cleaned for 5 minutes in a plasma cleaner (Harrick Plasma; Ithaca, N.Y.), then incubated for 20 minutes in piranha solution (H2O2:H2SO4::1:3). The substrate is then rinsed thoroughly in water and dried under nitrogen. Then, the glass coverslip is coated first with APTES. Bovine Serum Albumin (BSA; Sigma, St. Louis, Mo.) is then coated on top of the APTES layer by incubating the coverslip in a 1% solution (w/v in phosphate buffered saline, PBS) for 1 hour. After incubation with BSA solution, the coverslip is rinsed with water and dried under nitrogen. A laser system with a parameter set chosen to remove the BSA from the substrate (for example, the PALM system with laser power set to 60%, and scan speed of 20 µm/s, UV focus at 49, with a 40×0.6 NA objective) is used to ablate the BSA in a predefined pattern. Then, the ablated region is then backfilled with a biomolecule of interest. To backfill with laminin, for example, the substrate is incubated in a 0.1 mg/mL solution of laminin in PBS for 2 hours at 37 C. The substrate is then rinsed with water and dried under nitrogen.

The components of the present disclosure are described herein in terms of functional block components, flow charts and various processing steps. As such, it should be appreciated that such functional blocks are realized by any number of hardware and/or software components configured to perform the specified functions. For example, the present disclosure employs various integrated circuit components, e.g., memory elements, processing elements, logic elements, look-up tables, and the like, which may carry out a variety of functions under the control of one or more microprocessors or other control devices.

Similarly, the software elements of the present disclosure may be implemented with any programming or scripting language such as C, SQL, C++, Java, COBOL, assembler, PERL, or the like, with the various algorithms being implemented with any combination of data structures, objects, processes, routines or other programming elements. Further, it should be noted that the present disclosure may employ any number of conventional techniques for data transmission, signaling, data processing, network control, and the like as well as those yet to be conceived.

While this disclosure has been described as having exemplary embodiments, this application is intended to cover any variations, uses, or adaptations using the general principles set forth herein. It is envisioned that those skilled in the art may devise various modifications and equivalents without departing from the spirit and scope of the disclosure as recited in the following claims. Further, this application is intended to cover such departures from the present disclosure as come within the known or customary practice within the art to which it pertains.

DOCUMENTS CITED

Thery et al., Proc. Nat. Acad. Sci. USA. 2006. 103:19771-19776
Thery et al., Nat. Cell Biol. 2005. 7:947-953
Chen et al., Science. 1997. 276:1425-8.
Dike et al., 1999. In vitro Cell Dev. Biol. Anim. 35,441-448
Ingber, 1992. Semin Cancer Biol. 3:57-63.
Berg et al. Langmuir. 2004. 20:1362-8.
Recknor et al., Biomaterials. 2006 August; 27(22):4098-108.
Shannon, C. E. (1948), "A Mathematical Theory of Communication"
Bell, System Technical Journal, 27, pp. 379-423 & 623-656, July & October, 1948.

The invention claimed is:

1. A method for patterning one or more biomolecules on a substrate, the method comprising:
coating the substrate with the one or more biomolecules;
applying a focused laser onto the one or more biomolecules; and
ablating a portion of the one or more biomolecules with the laser in a predetermined pattern, the predetermined pattern having one or more ablated portions and one or more non-ablated portions on the substrate, the one or more ablated portions having one or more predetermined ranges of biological function or activity from less than 100% functional or less than 100% active to 0% functional or 0% active or the one or more ablated portions having one or more predetermined ranges of biochemical function or activity from less than 100% functional or less than 100% active to 0% functional or 0% active, and the one or more non-ablated portions having one or more active or functional biomolecules of the one or more biomolecules on the substrate; and wherein one or more ablated portions having at least one dimension in the plane of the substrate from at least about 0.1 nanometer, at least about 1 nanometer, at least about 10 nanometers, at least about 100 nanometers, or at least about 250 nanometers to about 1 meter; and the one or more non-ablated portions having at least one dimension in the plane of the substrate from at least about 0.1 nanometer, at least about 1 nanometer, at least about 10 nanometers, at least about 100 nanometers, or at least about 250 nanometers to about 1 meter.

2. The method of claim 1, wherein the ablating comprises breaking at least one covalent bond of the one or more biomolecules.

3. The method of claim 1, wherein ablating comprises ablating a portion of the one or more biomolecules with the laser in the predetermined pattern by removing at least one atom from one or more biomolecules and at most 100% of the atoms of one or more biomolecules, wherein the ablating of the one or more biomolecules does not substantially destroy or damage the one or more biomolecules or remove the one or more biomolecules to a depth of more than 1 nanometer, more than 3 nanometers, more than 5 nanometers, more than 10 nanometers, more than 25 nanometers, more than 50 nanometers, more than 100 nanometers, more than 500 nanometers, more than 1 micrometer, more than 5 micrometers, more than 10 micrometers, more than 50 micrometers, or more than 100 micrometers from a point in an area irradiated by the laser.

4. The method of claim 1, wherein applying the laser further comprises positioning the substrate in one, two, or three dimensions to form the predetermined pattern.

5. The method of claim 1, wherein the one or more biomolecules are selected from the group consisting of proteins, peptides, nucleic acids, drugs, lipids, bioactive polymers, bioactive compounds, and any combination thereof.

6. The method of claim 1, wherein the one or more of biomolecules are attached to a particle or colloid selected from the group consisting of quantum dots, superparamagnetic nanoparticles, dendrimers, glass or silica particles, liposomes, viruses or phage particles and analogous particles, and any combination thereof.

7. The method of claim 1, wherein the substrate is selected from the group consisting of glass, polymeric material, silicon, plastic, rubber, metal, ceramic, any material that is not substantially destroyed or damaged by the laser, and any combination thereof, and wherein the any material that is not substantially destroyed or damaged by the laser comprises material that is not substantially destroyed or damaged when laser irradiation of an area of substrate removes material to a depth of more than 1 nanometer, more than 3 nanometer, more than 5 nanometers, more than 10 nanometers, more than 25 nanometers, more than 50 nanometers, more than 100 nanometers, more than 500 nanometers, more than 1 micrometer, more than 5 micrometers, more than 10 micrometers, more than 50 micrometers, or more than 100 micrometers from a point in an area irradiated by the laser.

8. The method of claim 1, wherein coating the substrate comprises attaching the one or more biomolecules on the substrate by a method selected from the group consisting of covalently attaching to the substrate, adsorbing to the substrate, attaching via a coupling molecule of varying length, electrostatically attaching to the substrate, hydrophobically attaching to the substrate, sterically attaching to the substrate, entropically attaching to the substrate, and any combination thereof.

9. The method of claim 1, wherein coating the substrate comprises coating a non-uniform or prepatterned substrate.

10. The method of claim 1, wherein the laser removes at least one of the one or more biomolecules at a first dose and inactivates at least one of the one or more biomolecules at a second dose, and wherein the second dose is lower than the first dose.

11. The method of claim 1, wherein ablating comprises patterning a portion of the one or more biomolecules of one type of biomolecule in a combination of two or more types of biomolecules.

12. The method of claim 1, wherein the predetermined pattern contains a gradient of inactivated biomolecules, a gradient of removed biomolecules, or a combination of gradients of inactivated and removed biomolecules.

13. The method of claim 1, wherein the substrate is translucent, wherein applying the laser comprises applying the laser through an exterior side of the substrate onto an opposing interior side of the substrate, wherein the interior side of the substrate has the one or more biomolecules applied thereon, and wherein said molecules are partially or fully ablated in the predetermined pattern.

14. The method of claim 1, further comprising backfilling the one or more ablated portions with a second one or more biomolecules.

15. The method of claim 1, wherein the one or more biomolecules are in a dry environment, hydrated by a layer of liquid, in an aqueous solvent environment, or in a non-aqueous solvent environment.

\* \* \* \* \*